United States Patent
McKie et al.

(10) Patent No.: US 7,247,646 B2
(45) Date of Patent: Jul. 24, 2007

(54) BENZOPYRANONE COMPOUNDS, COMPOSITIONS THEREOF, AND METHODS OF TREATMENT THEREWITH

(75) Inventors: Jeffrey A. McKie, San Diego, CA (US); Shripad S. Bhagwat, San Diego, CA (US); Johanne Renaud, Basil (CH); Martin Missbach, Basil (CH)

(73) Assignees: Signal Pharmaceuticals, LLC, San Diego, CA (US); Novartis AG, Basel (CH)

( * ) Notice: Subject to any disclaimer, the term of this patent is extended or adjusted under 35 U.S.C. 154(b) by 221 days.

(21) Appl. No.: 10/942,519

(22) Filed: Sep. 15, 2004

(65) Prior Publication Data
US 2005/0137231 A1  Jun. 23, 2005

Related U.S. Application Data

(60) Provisional application No. 60/503,295, filed on Sep. 15, 2003.

(51) Int. Cl.
C07D 405/12 (2006.01)
A61K 31/4025 (2006.01)
A61K 31/453 (2006.01)

(52) U.S. Cl. ........................ 514/320; 514/422; 546/196; 548/525

(58) Field of Classification Search ............... 546/196; 548/525; 514/320, 422
See application file for complete search history.

(56) References Cited

U.S. PATENT DOCUMENTS

| | | |
|---|---|---|
| 6,291,456 B1 | 9/2001 | Stein et al. |
| 6,331,562 B1 | 12/2001 | Bhagwat |
| 6,620,838 B1 | 9/2003 | McKie et al. |
| 2004/0225005 A1* | 11/2004 | Friedman et al. ........... 514/422 |

FOREIGN PATENT DOCUMENTS

WO   WO 00/39120   7/2000

OTHER PUBLICATIONS

Al-Saffar et al., 1996, "Assessment of the role of GM-CSF in the cellular transformation and the development of erosive lesions around orthopaedic implants", Am J Clin Pathol. 105(5):628-639.
Alonzi et al., 1998, "Interleukin 6 is required for the development of collagen-induced arthritis", J Exp Med. 187(4):461-468.
Barkhem et al., 1998, "Differential response of estrogen receptor alpha and estrogen receptor beta to partial estrogen agonists/antagonists", Mol Pharmacol. 54(1):105-112.
Bismar et al., 1995, "Increased cytokine secretion by human bone marrow cells after menopause or discontinuation of estrogen replacement", J Clin Endocrinol Metab. 80(11):3351-3355.
Bodine et al., 1998, "Estrogen receptor-alpha is developmentally regulated during osteoblast differentiation and contributes to selective responsiveness of gene expression", Endocrinology. 139(4):2048-2057.
Borsellino et al., "Therapeutic agents II (genes, gene components, antireceptors)," Proc. Annu. Meet. Am. Assoc. Cancer Res. 37(2801):410-411 (1996).
Brandenberger et al., 1998, "Estrogen receptor alpha (ER-alpha) and beta (ER-beta) mRNAs in normal ovary, ovarian serous cystadenocarcinoma and ovarian cancer cell lines: down-regulation of ER-beta in neoplastic tissues", J Clin Endocrinol Metab. 83(3):1025-1028.
Chen et al., 2001, "Molecular basis for the constitutive activity of estrogen-related receptor alpha-1", J Biol Chem. 276(30):28465-470.
Chung et al., 2002, "Resisitance to tamoxifen-induced apoptosis is associated with direct interaction between Her2/neu and cell membrane estrogen receptor in breast cancer", Int J Cancer. 97(3):306-312.
Clinton and Hua, 1997, "Estrogen action in human ovarian cancer", Crit Rev Oncol Hematol. 25(1):1-9.
Cooke et al., 1998, "Mechanism of estrogen action: lessons from the estrogen receptor-alpha knockout mouse", Biol Reprod. 59(3):470-475.
Couse et al., 1997, "Tissue distribution and quantitative analysis of estrogen receptor-alpha (ERalpha) and estrogen receptor-beta (ERbeta) messenger ribonucleic acid in the wild-type and ERalpha-knockout mouse", Endocrinology. 138(11):4613-4621.

(Continued)

*Primary Examiner*—Fiona T. Powers
(74) *Attorney, Agent, or Firm*—Jones Day

(57) ABSTRACT

Benzopyranone Compounds having the following structure:

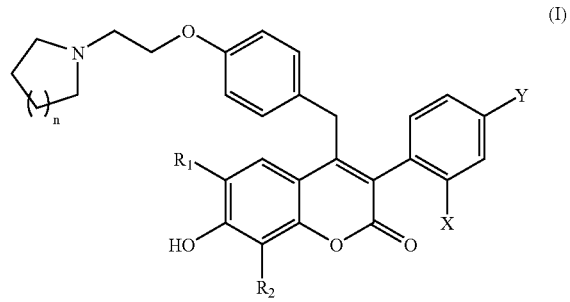

(I)

wherein $R_1$, $R_2$, X, Y and n are as defined herein, are disclosed. The Benzopyranone Compounds are useful for treating or preventing a bone-resorbing disease, a neoplastic disease, arthritis, a disease exacerbated by the presence of estrogen or a disease improved by the presence of estrogen, comprising administering an effective amount of a Benzopyranone Compound to a patient in need of the treating or preventing; activating the function of estrogen receptor ("ER") in a bone cell; inhibiting the function of ER in a cancer cell; inhibiting the expression of interleukin-6 ("IL-6") in a cell; and inhibiting the growth of a neoplastic cell, comprising contacting the cell with an effective amount of a Benzopyranone Compound.

4 Claims, No Drawings

OTHER PUBLICATIONS

Coward et al., 2001, "4-Hydroxytamoxifen binds to and deactivates the estrogen-related receptor gamma", Proc Natl Acad Sci U S A. 98(15):8880-8884.

Das et al., 1997, "Estrogenic responses in estrogen receptor-α deficient mice reveal a distinct estrogen signaling pathway", Proc. Natl. Acad. Sci. USA 94:12786-12791.

Devlin et al., 1998, "IL-6 mediates the effects of IL-1 or TNF, but not PTHrP or 1,25(OH)2D3, on osteoclast-like cell formation in normal human bone marrow cultures", J Bone Miner Res. Mar. 1998; 13(3):393-399.

Duan et al., 1998, "Estrogen-induced c-fos protooncogene expression in MCF-7 human breast cancer cells: role of estrogen receptor Sp1 complex formation", Endocrinology. 139(4):1981-1990.

Enmark et al., 1997, "Human estrogen receptor beta-gene structure, chromosomal localization, and expression pattern", J Clin Endocrinol Metab. 82(12):4258-4265.

Eustace et al., 1993, "Interleukin-6 (IL-6) functions as an autocrine growth factor in cervical carcinomas in vitro", Gynecol Oncol. 50(1):15-19.

Farhat et al., 1996, "The vascular protective effects of estrogen", FASEB J. 10(5):615-624.

Garrett et al., 1997, "A murine of human myeloma bone disease", Bone 20(6):515-520.

Girasole et al., 1992, "17 beta-estradiol inhibits interleukin-6 production by bone marrow-derived stromal cells and osteoblasts in vitro: a potential mechanism for the antiosteoporotic effect of estrogens", J Clin Invest. 89(3):883-891.

Grese et al., 1997, "Structure-activity relationships of selective estrogen receptor modulators: modifications to the 2-arylbenzothiophene core of raloxifene", J Med Chem. 40(2):146-167.

Gupta et al., 1985, "7-hydroxy-4-phenyl-3(4-hydroxyohenyl)-coumarin—a new interceptive agent", Indian J Exp Biol. 23(11):638-640.

Gustafsson et al., 1998, "Therapeutic potential of selective estrogen receptor modulators", Curr Opin Chem Biol. 2(4):508-511.

Hata et al., 1998, "Role estrogen and estrogen-related growth factor in the mechanism of hormone dependency of endometrial carcinoma cells", Oncology. 55 Suppl 1:35-43.

Hughes et al., 1996, "Estrogen promotes apoptosis of murine osteoclasts mediated by TGF-beta", Nat Med. 2(10):1132-1136.

Iafrati et al., 1997, "Estrogen inhibits the vascular injury response in estrogen receptor alpha-deficient mice", Nat Med. 3(5):545-548.

Jansson et al., 1994, "Estrogen induces a potent suppression of experimental autoimmune encephalomyelitis and collagen-induced arthritis in mice", J Neuroimmunol. 53(2):203-207.

Jeltsch et al., 1987, "Structure of the human oestrogen-responsive gene pS2", Nucleic Acids Res. 15(4):1401-1414.

Jilka et al., 1995, "Estrogen loss upregulates hematopoiesis in the mouse: a mediating role of IL-6", Exp Hematol. 23(6):500-506.

Jilka et al., 1992, "Increased osteoclast development after estrogen loss: mediation by interleukin-6", Science 57(5066):88-91.

Kelly et al., 1999, "Estrogen Modulation of G-protein-coupled Receptors", Trends Endocrinol Metab. 10(9):369-374.

Kimble et al., 1996, "Estrogen deficiency increases the ability of stromal cells to support murine osteoclastogenesis via an interleukin-1 and tumor necrosisfactor-mediatedstimulation of macrophage colony-stimulating factor production", J Biol Chem. 271(46):28890-28897.

Kimble et al., 1995, "Simultaneous block of interleukin-1 and tumor necrosis factor is required to completely prevent bone loss in the early postovariectomy period", Endocrinology. 136(7):3054-3061.

Klein et al., 1991, "Murine anti-interleukin-6 monoclonal antibody therapy for a patient with plasma cell leukemia", Blood. 78(5):1198-1204.

Klein et al., 1989, "Paracrine rather than autocrine regulation of myeloma-cell growth and differentiation by Interleukin-6", Blood. 73(2):517-526.

Koo et al., 1992, " Interleukin-6 and renal cell cancer: production, regulation, and growth effects", Cancer Immunol Immunother. 35(2):97-105.

Korach et al., 1994, "Insights from the study of animals lacking functional estrogen receptor", Science 266(5190):1524-1527.

Krege et al., 1998, "Generation and reproductive phenotypes of mice lacking estrogen receptor beta", Proc Natl Acad Sci U S A.95(26):15677-15682.

Kuiper et al., 1997, "Comparison of the ligand binding specificity and transcript tissue distribution of estrogen receptors alpha and beta", Endocrinology. Mar. 1997;138(3):863-870.

Kurihara et al., 1989, "Generation of osteoclasts from isolated hematopoietic progenitor cells", Blood 74(4):1295-1302.

Laflamme et al., 1998, "Expression and neuropeptidergic characterization of estrogen receptors (ERalpha and ERbeta) throughout the rat brain: anatomical evidence of distinct roles of each subtype", J Neurobiol. 36(3):357-378.

Lednicer et al., 1965, "Mammalian Antifertility Agents: Basic Ethers of 3,4—Diphenylcoumarin", J. Med. Chem. 8:725-726.

Leisten Interleukin-6 serum levels correlate with footpad swelling in adjuvant-induced arthritic Lewis rats treated with cyclosporin A or indomethacin. Clin Immunol Immunopathol. Jul. 1990;56(1):108-115.

Levin et al., 1999, "Cellular Functions of the Plasma Membrane Estrogen Receptor", Trends Endocrinol Metab. 10(9):374-377.

Lorenzo et al., 19887, "Colony-stimulating factors regulate the development of multinucleated osteoclasts from recently replicated cells in vitro", J Clin Invest. 80(1):160-164.

Lu et al., 2001, "Transcriptional regulation of the estrogen-inducible pS2 breast cancer marker gene by the ERR family of orphan nuclear receptors", Cancer Res. 15;61(18):6755-6761.

MacDonald et al., 1986, "Effects of human recombinant CSF-GM and highly purified CSF-1 on the formation of multinucleated cells with osteoclast characteristics in long-term bone marrow cultures", J Bone Miner Res. 1(2):227-233.

Martinez-Maza et al., 1992, "IL6 and AIDS", Res Immunol. 143(7):764-769.

Micheli et al., 1962, "Coumestrol, Plant Phenolics, and Synthetic Estrogen: a Correlation of Structure and Activity", 321-335.

Nadal et al., 2001, "The plasma membrane estrogen receptor: nuclear or unclear?", Trends Pharmacol Sci. 22(12):597-599.

Ogawa et al., 1997, "Behavioral effects of estrogen receptor gene disruption in male mice", Proc Natl Acad Sci U S A. 94(4):1476-1481.

Ohshima et al., 1998, "Interleukin 6 plays a key role in the development of antigen-induced arthritis", Proc. Natl. Acad. Sci. U S A. 95(14):8222-8226.

Okamoto et al., 1997, "Interleukin-6 as a paracrine and autocrine growth factor in human prostatic carcinoma cells in vitro", Cancer Res. 57(1):141-146.

Okamoto et al., 1997, "Autocrine effect of androgen on proliferation of an androgen responsive prostatic carcinoma cell line, LNCAP: role of interleukin-6", Endocrinology. 138(11):5071-5074.

Pacifici 1996, "Estrogen, cytokines, and pathogenesis of postmenopausal osteoporosis", J Bone Miner Res. 11(8):1043-1051.

Paech et al., 1997, "Differential ligand activation of estrogen receptors ERalpha and ERbeta at AP1 sites", Science. 277(5331):1508-1510.

Parfitt et al., 1996, "A new model for the regulation of bone resorption, with particular reference to the effects of bisphosphonates", J Bone Miner Res. 11(2):150-159.

Passeri et al., 1993, "Increased interleukin-6 production by murine bone marrow and bone cells after estrogen withdrawal", Endocrinology. 133(2):822-828.

Poli et al., 1994, "Interleukin-6 deficient mice are protected from bone loss caused by estrogen depletion", EMBO J. 13(5):1189-1196.

Pollard et al., 1968, "The oestrogenic and anti-oestrogenic activity of some synthetic steroids and non-steroids", Steroids 11(6):897-907.

Ray et al., 1987, "Enhanced antifertility activity of non-steroidal molecules with 3-n-butylamino-2-hydroxypropyloxy side chain", Contraception.35(3):283-287.

Reddy et al., 1994, "Interleukin-6 antisense deoxyoligonucleotides inhibit bone resorption by giant cells from human giant cell tumors of bone", J Bone Miner Res. 9(5):753-757.

Rissman et al., 1997, "Estrogen receptors are essential for female sexual receptivity", Endocrinology 138(1):507-510.

Rissman et al., 1997, "Estrogen receptor function as revealed by knockout studies: neuroendocrine and behavioralaspects", Horm Behav. 31(3):232-243.

Rohlff et al., 1998, "Prostate cancer cell growth inhibition by tamoxifen is associated with inhibition of protein kinase C and induction of p21(waf1/cip1)", Prostate. 37(1):51-59.

Sar et al., 1999, "Differential expression of estrogen receptor-beta and estrogen receptor-alpha in the rat ovary", Endocrinology. 140(2):963-971.

Schiller et al., 1997, " 17Beta-estradiol antagonizes effects of 1alpha,25-dihydroxyvitamin D3 on interleukin-6 production and osteoclast-like cell formation in mouse bone marrow primary cultures", Endocrinology 138(11):4567-4571.

Shinar et al., 1990, "The effect of hemopoitic growth factors on the generation of osteoclast-like cells in mouse bone marrow cultures", Endocrinology 126(3):1728-1735.

Shughrue et al., 1997, "Responses in the brain of estrogen receptor alpha-disrupted mice", Proc Natl Acad Sci USA 94(20):11008-11012.

Shughrue et al., 1997, "The distribution of estrogen receptor-beta mRNA in forebrain regions of the estrogen receptor-alpha knockout mouse", Endocrinology. 138(12):5649-5652.

Shughrue et al., 1997, "Comparative distribution of estrogen receptor-alpha and -beta mRNA in the rat central nervous system", J Comp Neurol. 388(4):507-525.

Siegall et al., 1990 "Expression of the interleukin 6 receptor and interleukin 6 in prostate carcinoma cells", Cancer Res. 50(24):7786-7788.

Simpson et al., 1998, "Estrogen regulation of transforming growth factor-alpha in ovarian cancer", J Steroid Biochem Mol Biol. 64(3-4):137-145.

Stein et al., 1995, "Repression of the interleukin-6 promoter by estrogen receptor is mediated by NF-Kappa B and C/EBP beta", Mol Cell Biol. 15(9):4971-4979.

Suzuki et al., 1996, "Calcitonin-induced changes in the cytoskeleton are mediated by a signal pathway associated with protein kinase A in osteoclasts", Endocrinology. 137(11):4685-4690.

Tartour et al., 1994, "Analysis of interleukin 6 gene expression in cervical neoplasia using a quantitative polymerase chain reaction assay: evidence for enhanced interleukin 6 gene expression in invasive carcinoma", Cancer Res. 54(23):6243-6248.

Tremblay et al., 2001, 4-Hydroxytamoxifen is an isoform-specific inhibitor of orphan estrogen-receptor-related (ERR) nuclear receptors beta and gamma. Endocrinology 142(10):4572-5.

Tremblay et al., 1998, "EM-800, a novel antiestrogen, acts as a pure antagonist of the transcriptional functions of estrogen receptors alpha and beta", Endocrinology 139(1):111-118.

Tsukamoto et al., 1992, "Interleukin-6 in renal cell carcinoma", J. Urol. 148(6):1778-81; discussion 1781-1782.

Turner et al., 1998, "Differential responses of estrogen target tissues in rats including bone to clomiphene, enclomiphene, and zuclomiphene", Endocrinology. 139(9):3712-3720.

Verma et al., 1993, "Microwave induced alteration in the neuron specific enolase gene expression", Indian J. Chem. 32B:239-243.

Weissglas et al., 1997, "The role of interleukin-6 in the induction of hypercalcemia in renal cell carcinoma transplanted into nude mice", Endocrinology 138(5):1879-1885.

Wendling et al., 1993, "Treatment of severe rheumatoid arthritis by anti-interleukin 6 monoclonal antibody", J Rheumatol. 20(2):259-262.

Wyckoff et al., 2001, "Plasma membrane estrogen receptors are coupled to endothelial nitric-oxide synthase through Galpha(i)", J Biol Chem. 276(29):27071-27076.

Yamashita et al., 1998, "Endocrine therapy in pancreatic carcinoma", Oncology. 55 Suppl 1:17-21.

Zhang et al., 1989, "Interleukin-6 is a potent myeloma-cell growth factor in patients with aggressive multiple myeloma", Blood. 74(1):11-13.

* cited by examiner

BENZOPYRANONE COMPOUNDS, COMPOSITIONS THEREOF, AND METHODS OF TREATMENT THEREWITH

This application claims priority to U.S. provisional application No. 60/503,295, filed Sep. 15, 2003, which is incorporated by reference herein in its entirety.

1. FIELD OF THE INVENTION

This invention relates to Benzopyranone Compounds, compositions comprising an effective amount of a Benzopyranone Compound and methods for treating or preventing a bone-resorbing disease, a neoplastic disease, arthritis, a disease exacerbated by the presence of estrogen or a disease improved by the presence of estrogen, comprising administering an effective amount of a Benzopyranone Compound to a patient in need thereof; activating the function of estrogen receptor ("ER") in a bone cell; inhibiting the function of ER in a cancer cell; inhibiting the expression of interleukin-6 ("IL-6") in a cell; and inhibiting the growth of a neoplastic cell, comprising contacting the cell with an effective amount of a Benzopyranone Compound.

2. BACKGROUND OF THE INVENTION

The estrogen hormone has a broad spectrum of effects on tissues in both females and males. Many of these biological effects are positive, including maintenance of bone density, cardiovascular protection, central nervous system ("CNS") function, and the protection of organ systems from the effects of aging. However, in addition to its positive effects, estrogen also is a potent growth factor in the breast and endometrium that increases the risk of cancer.

Until recently, it was assumed that estrogen binds to a single ER in cells. As discussed below, this simple view changed significantly when a second ER (ER-$\beta$) was cloned (with the original ER being renamed ER-$\alpha$), and when co-factors that modulate the ER response were discovered. Ligands can bind to two different ERs which, in the presence of tissue-specific co-activators and/or co-repressors, bind to an estrogen response element in the regulatory region of genes or to other transcription factors. Given the complexity of ER signaling, along with the tissue-specific expression of ER-$\alpha$ and ER-$\beta$ and their co-factors, it is now recognized that ER ligands can act as estrogen agonists and antagonists that mimic the positive effects, or block the negative effects, of estrogen in a tissue-specific manner. This has given rise to the discovery of an entirely new class of drugs, referred to as Selective Estrogen Receptor Modulators or SERMs. These drugs have significant potential for the prevention and/or treatment of cancer and osteoporosis, as well as cardiovascular diseases and neurodegenerative diseases such as Alzheimer's disease.

Bone-resorbing diseases, such as osteoporosis, are debilitating conditions which affect a wide population, and to which there is only limited treatment. For example, osteoporosis affects about 50% of women, and about 10% of men, over the age of 50 in the United States. In individuals with osteoporosis, increased loss of bone mass results in fragile bones and, as a result, increased risk of bone fractures. Other bone-resorption diseases, such as Paget's disease and metastatic bone cancer, present similar symptoms.

Bone is a living tissue which contains several different types of cells. In healthy individuals, the amount of bone made by the osteoblastic cells is balanced by the amount of bone removed or resorbed by the osteoclastic cells. In individuals suffering from a bone-resorbing disease, there is an imbalance in the function of these two types of cells. Perhaps the most well known example of such an imbalance is the rapid increase in bone resorption experienced by postmenopausal women. Such accelerated bone lose is attributed to estrogen deficiency associated with menopause. However, the mechanism of how the loss of estrogen results in increased bone resorption has long been debated.

Recently, investigators have suggested that an increase in bone-resorbing cytokines, such as interleukin-1 ("IL-1") and tumor necrosis factor ("TNF"), may be responsible for postmenopausal bone loss (Kimble et al., *J. Biol. Chem.* 271:28890–28897, 1996), and that inhibitors of these cytokines can partially diminish bone loss following ovariectomy in rodents (Pacifici, *J. Bone Miner Res.* 11:1043–1051, 1996). Further, discontinuation of estrogen has been reported to lead to an increase in IL-6 secretion by murine bone marrow and bone cells (Girasole et al., *J. Clin. Invest.* 89:883–891, 1992; Jilka et al., *Science* 257:88–91, 1992; Kimble et al., *Endocrinology* 136:3054–3061, 1995; Passeri et al., *Endocrinology* 133:822–828, 1993), antibodies against IL-6 can inhibit the increase in osteoclast precursors occurring in estrogen-depleted mice (Girasole et al, supra), and bone loss following ovariectomy does not occur in transgenic mice lacking IL-6 (Poli et al., *EMBO J.* 13:1189–1196, 1994).

Existing treatments for slowing bone loss generally involves administration of compounds such as estrogen, bisphosphonates, calcitonin, and raloxifene. These compounds, however, are generally used for long-term treatments, and have undesirable side effects. Further, such treatments are typically directed to the activity of mature osteoclasts, rather than reducing their formation. For example, estrogen induces the apoptosis of osteoclasts, while calcitonin causes the osteoclasts to shrink and detach from the surface of the bone (Hughes et al., *Nat. Med.* 2:1132–1136, 1996; Jilka et al., *Exp. Hematol.* 23:500–506, 1995). Similarly, bisphosphonates decrease osteoclast activity, change their morphology, and increase the apoptosis of osteoclasts (Parfitt et al., *J. Bone Miner Res.* 11:150–159, 1996; Suzuki et al., *Endocrinology* 137:4685–4690, 1996).

Cytokines are also believed to play an important role in a variety of cancers. For example, in the context of prostate cancer, researchers have shown IL-6 to be an autocrine/paracrine growth factor (Seigall et al., *Cancer Res.* 50:7786, 1999), to enhance survival of tumors (Okamoto et al., *Cancer Res.* 57:141–146, 1997), and that neutralizing IL-6 antibodies reduce cell proliferation (Okamoto et al., *Endocrinology* 138:5071–5073, 1997; Borsellino et al., *Proc. Annu. Meet. Am. Assoc. Cancer Res.* 37:A2801, 1996). Similar results have been reported for IL-6 with regard to multiple myeloma (Martinez-Maza et al., *Res. Immunol.* 143:764–769, 1992; Kawano et al., *Blood* 73:517–526, 1989; Zhang et al., *Blood* 74:11–13, 1989; Garrett et al., *Bone* 20:515–520, 1997; and Klein et al., *Blood* 78:1198-12–4, 1991), renal cell carcinoma (Koo et al., *Cancer Immunol.* 35:97–105, 1992; Tsukamoto et al., *J. Urol.* 148:1778–1782, 1992; and Weissglas et al., *Endocrinology* 138:1879–1885, 1997), and cervical carcinoma (Estuce et al., *Gynecol. Oncol.* 50:15–19, 1993; Tartour et al., *Cancer Res.* 54:6243–6248, 1994; and Iglesias et al., *Am. J. Pathology* 146:944–952, 1995).

Furthermore, IL-6 is also believed to be involved in arthritis, particularly in adjuvant-, collagen- and antigen-induced arthritis (Alonzi et al., *J. Exp. Med.* 187:146–148, 1998; Ohshima et al., *Proc. Natl. Acad. Sci. USA* 95:8222–8226, 1998; and Leisten et al., *Clin. Immunol.*

*Immunopathol* 56:108–115, 1990), and anti-IL-6 antibodies have been reported for treatment of arthritis (Wendling et al., *J. Rheumatol.* 20:259–262, 1993). In addition, estrogen has been shown to induce suppression of experimental autoimmune encephalomyelitis and collagen-induced arthritis in mice (Jansson et al., *Neuroimmunol.* 53:203–207, 1994).

The cytokine IL-6 has also been shown to be an important factor in inducing the formation of osteoclasts (Girasole et al., supra; Jilka et al. (1992), supra; Jilka et al. (1995), supra; Kimble et al. (1995), supra; Pacifici et al., supra; and Passeri et al., supra). Other investigators have shown that administration of the neutralizing antibody, antisense oligos, or the Sant 5 antagonist against IL-6, reduces the number of osteoclasts in trabecular bone of ovariectomized mice (Devlin et al., *J. Bone Miner* 13:393–399, 1998; Girasole et al., supra; Jilka et al. (1992), supra; and Schiller et al., *Endocrinology* 138:4567–4571, 1997), the ability of human giant cells to resorb dentine (Ohsaki et al., *Endocrinology* 131:2229–2234, 1993; and Reddy et al., *J. Bone Min. Res.* 9:753–757, 1994), and the formation of osteoclasts in normal human bone marrow culture. It has also been found that estrogen downregulates the IL-6 promoter activity by interactions between the estrogen receptor and the transcription factors NF-κB and C/EBPβ (Stein et al., *Mol. Cell Biol.* 15:4971–4979, 1995).

Granulocyte-macrophage colony-stimulating factor ("GM-CSF") has been suggested to play a role in the proliferation of osteoclastic precursor cells. In long term cultures of human or mouse bone marrow cells or peripheral blood cells, GM-CSF promotes the formation of osteoclastic cells (Kurihara et al., *Blood* 74:1295–1302, 1989; Lorenzo et al., *J. Clin. Invest.* 80:160–164, 1987; MacDonald et al., *J. Bone Miner* 1:227–233, 1986; and Shinar et al, *Endocrinology* 126:1728–1735, 1990). Bone marrow cells isolated from postmenopausal women, or women who discontinued estrogen therapy, expressed higher levels of GM-CSF than cells from premenopausal women (Bismar et al., *J. Clin. Endocrinol. Metab.* 80:3351–3355, 1995). Expression of GM-CSF has also been shown to be associated with the tissue distribution of bone-resorbing osteoclasts in patients with erosion of orthopedic implants (Al-Saffar et al., *Anatomic Pathology* 105:628–693, 1996).

As noted above, it had previously been assumed that estrogen binds to a single ER in cells, causing conformational changes that result in release from heat shock proteins and binding of the receptor as a dimer to the so-called estrogen response element in the promoter region of a variety of genes. Further, pharmacologists have generally believed that non-steroidal small molecule ligands compete for binding of estrogen to ER, acting as either antagonists or agonists in each tissue where the estrogen receptor is expressed. Thus, such ligands have traditionally been classified as either pure antagonists or agonists. This is no longer believed to be correct.

Rather, it is now known that estrogen modulates cellular pharmacology through gene expression, and that the estrogen effect is mediated by estrogen receptors. As noted above, there are currently two estrogen receptors, ER-α and ER-β. The effect of estrogen receptor on gene regulation can be mediated by a direct binding of ER to the estrogen response element (ERE)—"classical pathway" (Jeltsch et al., *Nucleic Acids Res.* 15:1401–1414, 1987; Bodine et al., *Endocrinology* 139:2048–2057, 1998), binding of ER to other transcription factors such as NF-κB, C/EBP-β or AP-1—"non-classical pathway" (Stein et al., *Mol. Cell Biol.* 15:4971–4979, 1995; Paech et al., *Science* 277:1508–1510, 1997; Duan et al., *Endocrinology* 139:1981–1990, 1998), and through non-genomic effects via extranuclear estrogen receptor signaling that potentially include plasma membrane ER (Nadal, A. et al., *Trends in Pharmacological Sciences* 22:597–599, 2001; Wyckoff, M. H. et al., *J. Biol. Chem.* 276:27071–27076, 2001; Chung, Y-L. et al., *Int. J. of Cancer* 97:306–312, 2002; Kelly, M. J. et al., *Trends Endocrinol. Metab.* 10:369–374, 1999; Levin, E. R. et al., *Trends Endocrinol. Metab.* 10:374–377, 1999).

Progress over the last few years has shown that ER associates with co-activators (e.g., SRC-I, CBP and SRA) and co-repressors (e.g., SMRT and N-CoR), which also modulate the transcriptional activity of ER in a tissue-specific and ligand-specific manner. In such cases, ER interacts with the transcription factors critical for regulation of these genes. Transcription factors known to be modulated in their activity by ER include, for example, AP-1, NF-κB, C/EBP and Sp-1. In addition, orphan nuclear receptors, such as estrogen receptor-related receptors a, b, g (ERR-a, ERR-b, ERR-g), have been identified. Although estradiol does not appear to be a ligand for the ERRs, some SERMs and other traditional ER-ligands have been shown to bind to the receptors with high affinity (Coward, P. et al., *Proc. Natl. Acad. Sci.* 98:8880–8884, 2001; Lu, D. et al., *Cancer Res.* 61:6755–6761, 2001; Tremablay, G. B. et al., *Endocrinology* 142:4572–4575, 2001; Chen, S. et al., *J. Biol. Chem.* 276:28465–28470, 2001).

Furthermore, ER-α and ER-β have both overlapping and different tissue distributions, as analyzed predominantly by RT-PCR or in-situ hybridization due to a lack of good ER-β antibodies. Some of these results, however, are controversial, which may be attributable to the method used for measuring ER, the species analyzed (rat, mouse, human) and/or the differentiation state of isolated primary cells. Very often tissues express both ER-α and ER-β, but the receptors are localized in different cell types. In addition, some tissues (such as kidney) contain exclusively ER-α, while other tissues (such as uterus, pituitary and epidymis) show a great predominance of ER-α (Couse et al., *Endocrinology* 138, 4613–4621, 1997; Kuiper et al., *Endocrinology* 138, 863–870, 1997). In contrast, tissues expressing high levels of ER-β include prostate, testis, ovaries and certain areas of the brain (Brandenberger et al., *J. Clin. Endocrinol. Metab.* 83, 1025–8, 1998; Enmark et al., *J. Clinic. Endocrinol. Metabol.* 82, 4258–4265, 1997; Laflamme et al., *J. Neurobiol.* 36, 357–78, 1998; Sar and Welsch, *Endocrinology* 140, 963–71, 1999; Shughrue et al., *Endocrinology* 138, 5649–52, 1997a; Shughrue et al., *J. Comp. Neurol.* 388, 507–25, 1997b).

The development of ER-α (Korach, *Science* 266, 1524–1527, 1994) and ER-β (Krege et al., *Proc. Natl. Acad. Sci. USA* 95, 15677–82, 1998) knockout mice further demonstrate that ER-β has different functions in different tissues. For example, ER-α knockout mice (male and female) are infertile, females do not display sexual receptivity and males do not have typical male-aggressive behavior (Cooke et al., *Biol. Reprod.* 59, 470–5, 1998; Das et al., *Proc. Natl. Acad. Sci. USA* 94, 12786–12791, 1997; Korach, 1994; Ogawa et al., *Proc. Natl. Acad. Sci. USA* 94, 1476–81, 1997; Rissman et al., *Endocrinology* 138, 507–10, 1997a; Rissman et al., *Horm. Behav.* 31, 232–243, 1997b). Further, the brains of these animals still respond to estrogen in a pattern that is similar to that of wild-type animals (Shughrue et al., *Proc. Natl. Acad. Sci. USA* 94, 11008–12, 1997c), and estrogen still inhibits vascular injury caused by mechanical damage (Iafrati et al., *Nature Med.* 3, 545–8, 1997). In contrast, mice lacking the ER-β develop normally, are fertile and exhibit normal sexual behavior, but have fewer and smaller litters than wild-type mice (Krege et al., 1998), have normal breast development and lactate normally. The reduction in fertility is believed to be the result of reduced ovarian efficiency, and ER-β is the predominant form of ER in the ovary, being localized in the granulosa cells of maturing follicles.

In summary, compounds which serve as estrogen antagonists or agonists have long been recognized for their significant pharmaceutical utility in the treatment of a wide variety of estrogen-related conditions, including conditions related to the brain, bone, cardiovascular system, skin, hair follicles, immune system, bladder and prostate (Barkhem et al., *Mol. Pharmacol.* 54, 105–12, 1998; Farhat et al., *FASEB J.* 10, 615–624, 1996; Gustafsson, *Chem. Biol.* 2, 508–11, 1998; Sun et al., 1999; Tremblay et al., *Endocrinology* 139, 111–118, 1998; Turner et al., *Endocrinology* 139, 3712–20, 1998). In addition, a variety of breast and non-breast cancer cells have been described to express ER, and serve as the target tissue for specific estrogen antagonists (Brandenberger et al., 1998; Clinton and Hua, *Crit. Rev. Oncol. Hematol.* 25, 1–9, 1997; Hata et al., *Oncology* 55 *Suppl* 1, 35–44, 1998; Rohlff et al., *Prostate* 37, 51–9, 1998; Simpson et al., *J Steroid Biochem Mol Biol* 64, 137–45, 1998; Yamashita et al., *Oncology* 55 *Suppl* 1, 17–22, 1998).

In recent years a number of both steroidal and nonsteroidal compounds which interact with ER have been developed. For example, Tamoxifen was originally developed as an anti-estrogen and used for the treatment of breast cancer, but more recently has been found to act as a partial estrogen agonist in the uterus, bone and cardiovascular system. Raloxifene is another compound that has been proposed as a SERM, and has been approved for treatment of osteoporosis.

Tamoxifen

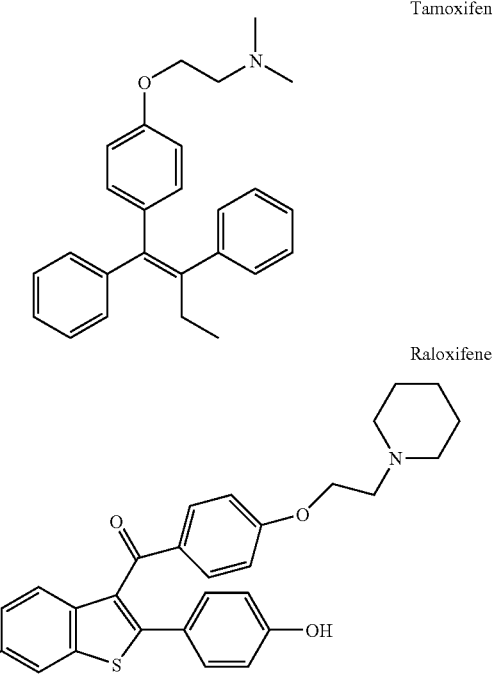

Raloxifene

Analogs of Raloxifene have also been reported (Grese et al., *J. Med. Chem.* 40:146–167, 1997).

As for coumarin-based compounds, a number of structures have been proposed, including the following: U.S. Pat. Nos. 6,291,456, 6,331,562 and 6,593,322; Roa et al., *Synthesis* 887–888, 1981; Buu-Hoi et al., *J. Org. Chem.* 19:1548–1552, 1954; Gupta et al., *Indian J. Exp. Biol.* 23:638–640, 1985; Published PCT Application No. WO 96/31206; Verma et al., *Indian J. Chem.* 32B:239–243, 1993; Lednicer et al., *J. Med. Chem.* 8:725–726, 1965; Micheli et al., *Steroids* 5:321–335, 1962; Brandt et al., *Int. J. Quantum Chemistry: Quantum Biol. Symposia* 13:155–165, 1986; Wani et al., *J. Med. Chem.* 18:982–985, 1975; Pollard et al., *Steroids* 11:897–907, 1968.

Accordingly, there is a need in the art for improved compounds useful for treating or preventing a bone-resorbing disease, a neoplastic disease, arthritis, a disease exacerbated by the presence of estrogen or a disease improved by the presence of estrogen; activating the function of ER in a bone cell; inhibiting the function of ER in a cancer cell; inhibiting the expression of IL-6 in a cell; and inhibiting the growth of a neoplastic cell.

Citation or identification of any reference in Section 2 of this application is not to be construed as an admission that the reference is prior art to the present application.

3. SUMMARY OF THE INVENTION

The invention relates to compounds having the following formula (I):

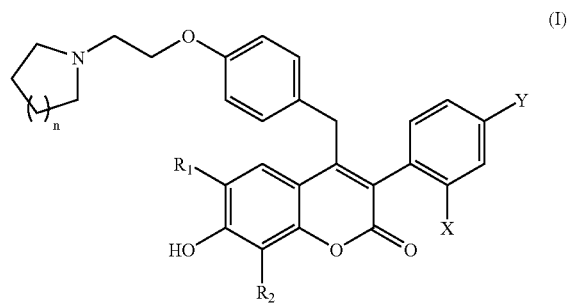

and pharmaceutically acceptable salts thereof,
wherein:
X and Y are independently hydrogen, halogen or (halo)($C_{1-6}$alkyl);
n is 1, 2 or 3; and
either:
(a) $R_1$ is hydrogen and $R_2$ is halogen, hydroxy, —($C_{1-6}$alkyl), vinyl, —($C_{2-6}$alkynyl), —C(O)O($C_{1-6}$alkyl), -(hydroxy)($C_{1-6}$alkyl), -(amino)($C_{1-6}$alkyl), —($CH_2$)$_m$—O—($C_{1-6}$alkyl), —C(O)($C_{1-6}$alkyl), —($CH_2$)$_m$-phenyl, -(3- to 7-membered monocyclic heterocycle), —COOH, —C(O)H or —CN;
(b) $R_2$ is hydrogen and $R_1$ is halogen, hydroxy, —($C_{1-6}$alkyl), —($C_{2-6}$alkenyl)-($C_{2-6}$alkynyl), —C(O)O($C_{1-6}$alkyl), -(hydroxy)($C_{1-6}$alkyl), -(amino)($C_{1-6}$alkyl), —($CH_2$)$_m$—O—($C_{1-6}$alkyl), —C(O)($C_{1-6}$alkyl), —($CH_2$)$_m$-phenyl, -(3- to 7-membered monocyclic heterocycle), —COOH, —C(O)H or —CN; or
(c) $R_1$ and $R_2$ are —$CH_3$.

A compound or a pharmaceutically acceptable salt of a compound of formula (I) (each being a "Benzopyranone Compound") is useful for treating or preventing a bone-resorbing disease, a neoplastic disease, arthritis, a disease exacerbated by the presence of estrogen or a disease improved by the presence of estrogen; activating the function of ER in a bone cell; inhibiting the function of ER in a cancer cell; inhibiting the expression of IL-6 in a cell; and inhibiting the growth of a neoplastic cell.

The invention also relates to compositions comprising an effective amount of a Benzopyranone Compound and a pharmaceutically acceptable carrier or vehicle. The compositions are useful for treating or preventing a bone-resorbing disease, a neoplastic disease, arthritis, a disease exacerbated by the presence of estrogen or a disease improved by the presence of estrogen; activating the function of ER in a bone cell; inhibiting the function of ER in a cancer cell; inhibiting the expression of IL-6 in a cell; and inhibiting the growth of a neoplastic cell.

The invention also relates to methods for making a Benzopyranone Compound, comprising demethylating a compound of formula (II):

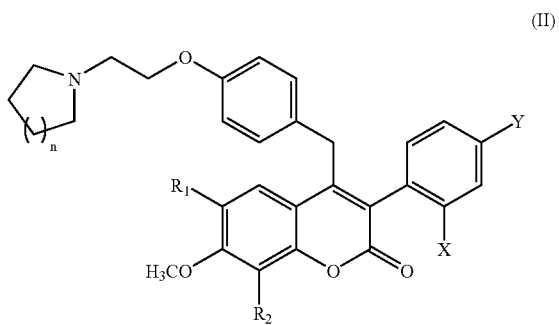

(II)

or a pharmaceutically acceptable salt thereof, wherein $R_1$, $R_2$, X, Y and n are as defined above for the Benzopyranone Compounds.

The invention further relates to methods for treating or preventing a bone-resorbing disease, comprising administering an effective amount of a Benzopyranone Compound to a patient in need of the treating or preventing.

The invention further relates to methods for treating or preventing a neoplastic disease, comprising administering an effective amount of a Benzopyranone Compound to a patient in need of the treating or preventing.

The invention further relates to methods for treating or preventing arthritis, comprising administering an effective amount of a Benzopyranone Compound to a patient in need of the treating or preventing.

The invention further relates to methods for treating or preventing a disease exacerbated by the presence of estrogen, comprising administering an effective amount of a Benzopyranone Compound to a patient in need of the treating or preventing.

The invention further relates to methods for treating or preventing a disease improved by the presence of estrogen, comprising administering an effective amount of a Benzopyranone Compound to a patient in need of the treating or preventing.

The invention further relates to methods for activating the function of ER in a bone cell, comprising contacting a bone cell with an effective amount of a Benzopyranone Compound.

The invention further relates to methods for inhibiting the function of ER in a cancer cell, comprising contacting the cell with an effective amount of a Benzopyranone Compound.

The invention further relates to methods for inhibiting the expression of IL-6 in a cell, comprising contacting a cell capable of expressing ER and IL-6 with an effective amount of a Benzopyranone Compound.

The invention further relates to methods for inhibiting growth of a neoplastic cell, comprising contacting a neoplastic cell capable of expressing ER with an effective amount of a Benzopyranone Compound.

The invention further relates to methods for treating or preventing endometriosis, a cardiovascular disease, hypercholesterolemia, prostatic hypertrophy, prostatic carcinoma, obesity, hot flashes, a skin effect, mood swings, memory loss, a menopausal syndrome, hair loss (alopecia), type-II diabetes, Alzheimer's disease, urinary incontinence, a GI tract condition, vascular protection after injury, a CNS effect, acne, cataracts, hirsutism, multiple myeloma or lymphoma comprising administering an effective amount of a compound or a pharmaceutically acceptable salt of the compound of claim 1 to a patient in need of the treating or preventing.

The invention further relates to methods for preventing spermatogenesis or an adverse reproductive effect associated with exposure to an environmental chemical or a natural hormonal imbalance comprising administering an effective amount of a Benzopyranone Compound to a patient in need of the preventing.

The present invention may be understood more fully by reference to the detailed description and examples, which are intended to exemplify non-limiting embodiments of the invention.

4. DETAILED DESCRIPTION OF THE INVENTION

4.1 Definitions

A "—$(C_{1-6}$alkyl)" group is a saturated straight chain or branched non-cyclic hydrocarbon having from 1 to 6 carbon atoms. Representative —($C_{1-6}$alkyls) include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2,3-dimethylbutyl and the like.

A "—($C_{2-6}$alkenyl)" group is a straight chain or branched non-cyclic hydrocarbon having from 2 to 6 carbon atoms, and including at least one carbon-carbon double bond. Representative —($C_{2-6}$alkenyl)s include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl and the like. The double bond of an alkenyl group can be unconjugated or conjugated to another unsaturated group.

A "vinyl" group is —CH═CH$_2$.

A "—($C_{2-6}$alkynyl)" group is a straight chain or branched non-cyclic hydrocarbon having from 2 to 6 carbon atoms, and including at least one carbon-carbon triple bond. Representative —($C_{2-6}$alkynyls) include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like. The triple bond of an alkynyl group can be unconjugated or conjugated to another unsaturated group.

Examples of a "—C(O)O($C_{1-6}$alkyl)" group, wherein —($C_{1-6}$alkyl) is defined above, include, but are not limited to, —C(O)OCH$_3$, —C(O)OCH$_2$CH$_3$, —C(O)O(CH$_2$)$_2$CH$_3$, —C(O)OCH(CH$_3$)CH$_3$ and the like.

Examples of a "—(CH$_2$)$_m$—O—($C_{1-6}$alkyl)" group, wherein —($C_{1-6}$alkyl) and m are defined above, include, but are not limited to, —O—CH$_3$, —CH$_2$—O—CH$_3$, —CH$_2$—

O—CH$_2$CH$_3$, —CH$_2$—O—(CH$_2$)$_2$CH$_3$, —(CH$_2$)$_2$—O—CH$_3$, —(CH$_2$)$_2$—O—CH$_2$CH$_3$ and the like.

Examples of a "—C(O)(C$_{1-6}$alkyl)" group, wherein —(C$_{1-6}$alkyl) is defined above, include, but are not limited to, —C(O)CH$_3$, —C(O)—CH$_2$CH$_3$, —C(O)—(CH$_2$)$_2$CH$_3$, —C(O)—(CH$_2$)$_3$CH$_3$, —C(O)—(CH$_2$)$_4$CH$_3$, —C(O)—(CH$_2$)$_5$CH$_3$ and the like.

Examples of a "—(CH$_2$)$_m$-phenyl" group, wherein m is defined above, include, but are not limited to, -phenyl, —CH$_2$-phenyl, —(CH$_2$)$_2$-phenyl, —(CH$_2$)$_3$-phenyl, —(CH$_2$)$_4$-phenyl, —(CH$_2$)$_5$-phenyl and the like.

A "3- to 7-membered monocyclic heterocycle" is a monocyclic group having at least one atom selected from O, N or S, and which has 2–6 carbon atoms, which may be saturated, unsaturated or aromatic, including (but not limited to) pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl.

An "-(amino)(C$_{1-6}$alkyl)" group is a C$_{1-6}$alkyl group defined above, substituted with one or two amino groups. Examples include, but are not limited to, —CH$_2$—NH$_2$, —CH$_2$CH$_2$NH$_2$, —(CH$_2$)$_3$NH$_2$, —(CH$_2$)$_4$NH$_2$, —(CH$_2$)$_5$NH$_2$, —CH$_2$—(NH$_2$)(CH$_2$)$_5$CH$_3$, —CH—(NH$_2$)(CH$_3$)$_2$, —CH—(NH$_2$)(CH$_2$CH$_3$)$_2$, —C—(NH$_2$)((CH$_2$)$_2$CH$_3$)$_2$, and the like.

A "-(hydroxy)(C$_{1-6}$alkyl)" group is a C$_{1-6}$alkyl group defined above, substituted with one or two hydroxy groups. Examples include, but are not limited to, —CH$_2$OH; —(CH$_2$)$_2$OH; —(CH$_2$)$_3$OH; —(CH$_2$)$_4$OH; —(CH$_2$)$_5$OH; —CH(OH)CH$_3$, —CH(OH)CH$_2$CH$_3$, —CH$_2$CH(OH)CH$_3$, and the like.

A "halogen" is fluorine, chlorine, bromine or iodine.

A "-(halo)(C$_{1-6}$alkyl)" is —(C$_{1-6}$alkyl) defined above substituted with one or more halogens. Examples include, but are not limited to, —CF$_3$, —CHF$_2$, —CH$_2$F, —CCl$_3$, —CHCl$_2$, —CBr$_3$, —CHBr$_2$, —CH$_2$CF$_3$, —CH$_2$CHF$_2$, —CH$_2$CH$_2$F, and the like.

The Benzopyranone Compounds can have chiral centers and can occur as racemates, individual enantiomers or diastereomers, and mixtures thereof. All such isomeric forms are included within the present invention, including mixtures thereof. Furthermore, some of the Benzopyranone Compounds can exist as polymorphs, which are included in the present invention. In addition, some of the Benzopyranone Compounds can also form solvates with water or other organic solvents. Such solvates are similarly included within the scope of this invention.

An estrogen "agonist" is a compound that binds to and activates the function of ER in one or more cells or tissues, while an estrogen "antagonist" binds to and inhibits the function of ER in one or more cells or tissues. ER includes ER-α, ER-β, an isoform or mutation of either, and a protein having at least 95% homology to ER.

The term "effective amount" in connection with a Benzopyranone Compound means an amount capable of: treating a bone-resorbing disease, a neoplastic disease, arthritis, a disease exacerbated by the presence of estrogen or a disease improved by the presence of estrogen; activating the function of ER in a bone cell; inhibiting the function of ER in a cancer cell; inhibiting the expression of IL-6 in a cell; or inhibiting the growth of a neoplastic cell.

The term "effective amount" in connection with another therapeutic agent means an amount capable of treating or preventing a bone-resorbing disease, a neoplastic disease, arthritis, a disease exacerbated by the presence of estrogen or a disease improved by the presence of estrogen; activating the function of ER in a bone cell; inhibiting the function of ER in a cancer cell; inhibiting the expression of IL-6 in a cell; or inhibiting the growth of a neoplastic cell, while the Benzopyranone Compound is exerting its therapeutic or prophylactic effect.

A "patient" is an animal, including, but not limited to, an animal such a cow, monkey, horse, sheep, pig, chicken, turkey, quail, cat, dog, mouse, rat, rabbit, and guinea pig, in one embodiment a mammal, in another embodiment a human.

4.2 Benzopyranone Compounds

The invention relates to Benzopyranone Compounds having the following formula: (I):

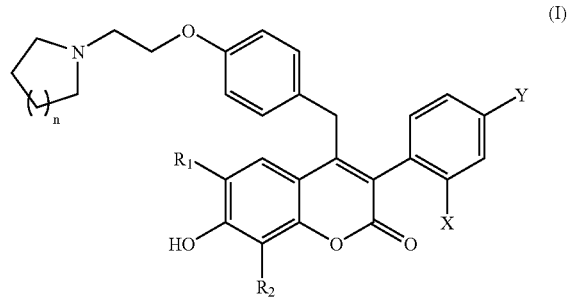

wherein $R_1$, $R_2$, X, Y and n are defined above.

In one embodiment, the Benzopyranone Compounds are those wherein $R_1$ is hydrogen.

In another embodiment, the Benzopyranone Compounds are those wherein $R_2$ is hydrogen.

In another embodiment, the Benzopyranone Compounds are those wherein both of $R_1$ and $R_2$ are —CH$_3$.

In another embodiment, the Benzopyranone Compounds are those wherein one of $R_1$ and $R_2$ is —C(O)—(C$_{1-6}$alkyl) and the other is hydrogen.

In another embodiment, the Benzopyranone Compounds are those wherein one of $R_1$ and $R_2$ is —C(O)H and the other is hydrogen.

In another embodiment, the Benzopyranone Compounds are those wherein one of $R_1$ and $R_2$ is methyl and the other is hydrogen.

In another embodiment, the Benzopyranone Compounds are those wherein $R_1$ is methyl and $R_2$ is hydrogen.

In another embodiment, the Benzopyranone Compounds are those wherein $R_2$ is methyl and $R_1$ is hydrogen.

In another embodiment, the Benzopyranone Compounds are those wherein one of $R_1$ and $R_2$ is CN and the other is hydrogen.

In another embodiment, the Benzopyranone Compounds are those wherein one of $R_1$ and $R_2$ is -(hydroxy)(C$_{1-6}$alkyl) and the other is hydrogen.

In another embodiment, the Benzopyranone Compounds are those wherein one of $R_1$ and $R_2$ is halogen and the other is hydrogen.

In another embodiment, the Benzopyranone Compounds are those wherein $R_1$ is —($C_{2-6}$alkenyl) and $R_2$ is hydrogen.

In another embodiment, the Benzopyranone Compounds are those wherein $R_2$ is vinyl and $R_1$ is hydrogen.

In another embodiment, the Benzopyranone Compounds are those wherein X and Y are both halogen.

In another embodiment, the Benzopyranone Compounds are those wherein X and Y are both chloro.

In another embodiment, the Benzopyranone Compounds are those wherein X and Y are both trifluoromethyl.

In another embodiment, the Benzopyranone Compounds are those wherein X is hydrogen and Y is trifluoromethyl.

In another embodiment, the Benzopyranone Compounds are those wherein X is trifluoromethyl and Y is chloro.

In another embodiment, the Benzopyranone Compounds are those wherein X is chloro and Y is trifluoromethyl.

In another embodiment, the Benzopyranone Compounds are those wherein X is hydrogen and Y is halogen.

In another embodiment, the Benzopyranone Compounds are those wherein one of $R_1$ and $R_2$ is —C(O)—($C_{1-6}$alkyl) and the other is hydrogen, and X and Y are both halogen, such as chloro.

In another embodiment, the Benzopyranone Compounds are those wherein one of $R_1$ and $R_2$ is methyl and the other is hydrogen, X and Y are both halogen, such as chloro.

In another embodiment, the Benzopyranone Compounds are those wherein one of $R_1$ and $R_2$ is methyl and the other is hydrogen, one of X and Y is trifluoromethyl and the other is hydrogen.

In another embodiment, the Benzopyranone Compounds are those wherein one of $R_1$ and $R_2$ is —C(O)—($C_{1-6}$alkyl) and the other is hydrogen, one of X and Y is trifluoromethyl and the other is hydrogen.

In another embodiment, the Benzopyranone Compounds are those wherein one of $R_1$ and $R_2$ is CN and the other is hydrogen, one of X and Y is trifluoromethyl and the other is hydrogen.

In another embodiment, the Benzopyranone Compounds are those wherein one of $R_1$ and $R_2$ is —CH(OH)—$CH_3$ and the other is hydrogen, one of X and Y is trifluoromethyl and the other is hydrogen.

In another embodiment, the Benzopyranone Compounds are those wherein one of $R_1$ and $R_2$ is halogen, such as bromo, and the other is hydrogen, one of X and Y is trifluoromethyl and the other is hydrogen.

In another embodiment, the Benzopyranone Compounds are those wherein one of $R_1$ and $R_2$ is halogen, such as iodo, and the other is hydrogen, one of X and Y is halogen, such as chloro, and the other is hydrogen.

In another embodiment, the Benzopyranone Compounds are those wherein $R_1$ is —$CH_2$—CH=$CH_2$, $R_2$ is hydrogen, one of X and Y is trifluoromethyl and the other is hydrogen.

In another embodiment, the Benzopyranone Compounds are those wherein $R_2$ is vinyl, $R_1$ is hydrogen, one of X and Y is trifluoromethyl and the other is hydrogen.

In another embodiment, the Benzopyranone Compounds are those wherein one of $R_1$ and $R_2$ is —$CH_2$—$NH_2$ and the other is hydrogen, one of X and Y is halogen, such as chloro, and the other is hydrogen.

In another embodiment, the Benzopyranone Compounds are those wherein n is 1.

4.3 Methods for Making Benzopyranone Compounds

The Benzopyranone Compounds can be prepared according to the general reactions in Schemes 1–23 shown below as well as in Examples 1–9.

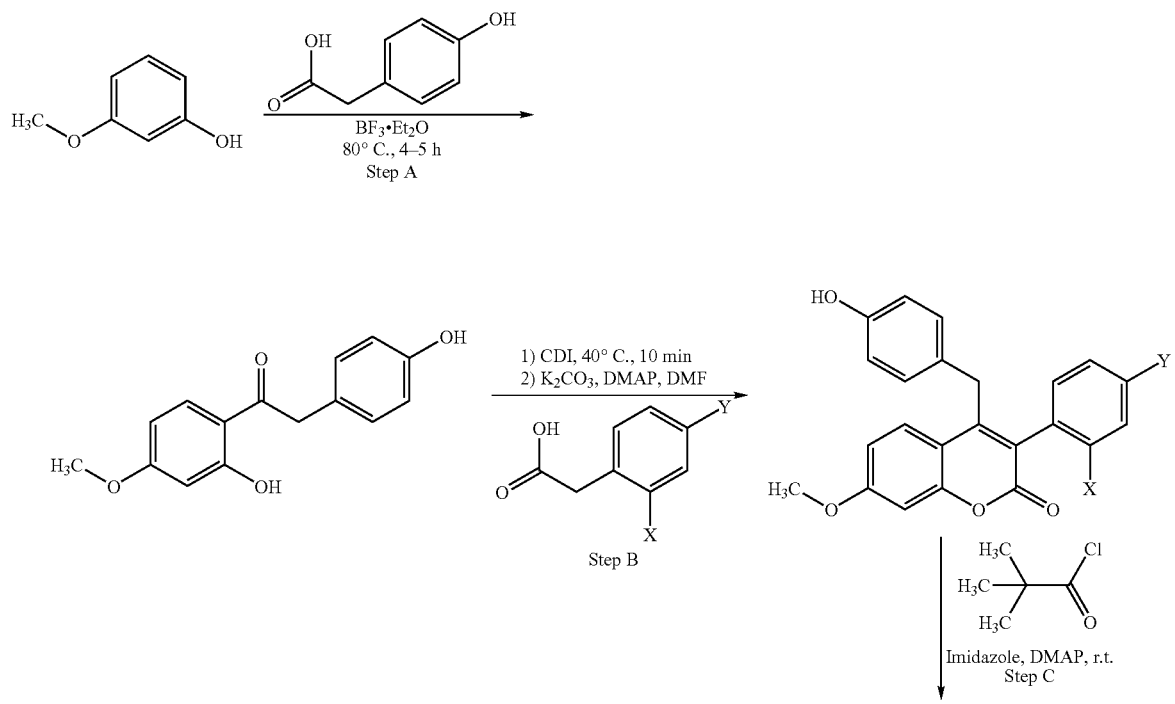

Scheme 1:

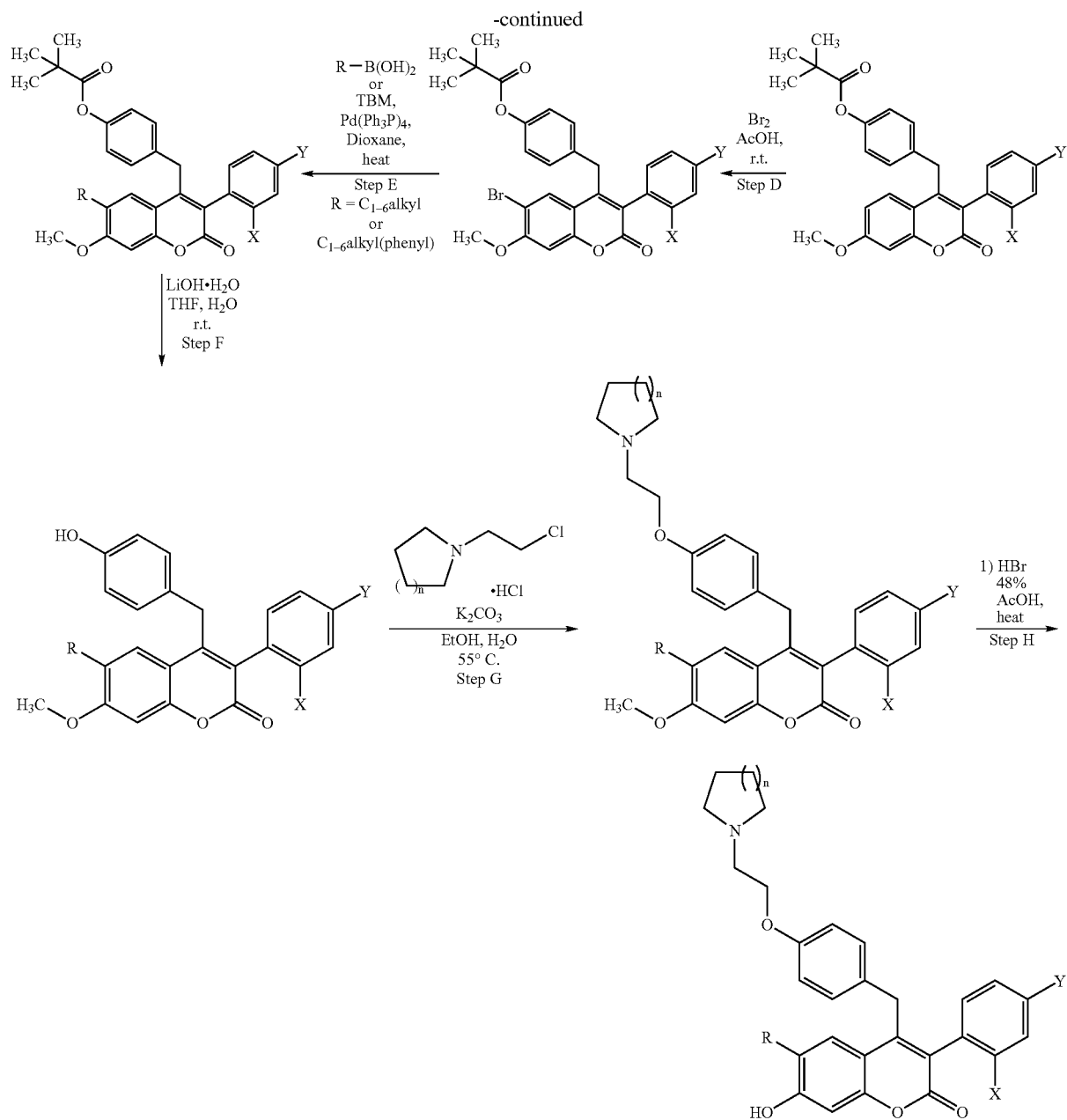
Illustrative examples of steps A–H in Scheme 1, above, are set forth in Example 1, below.
Scheme 2:
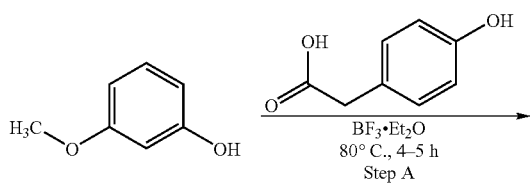

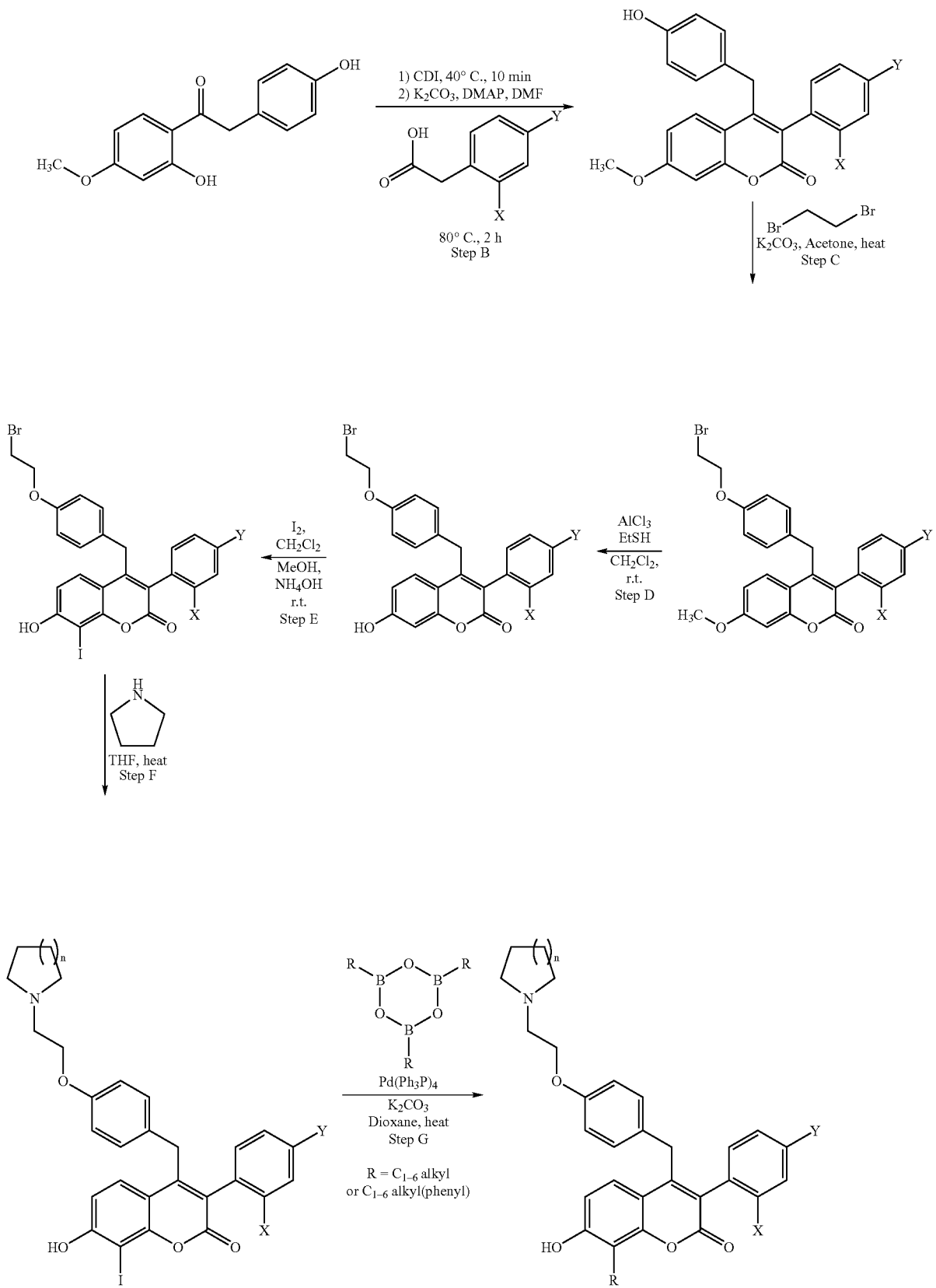

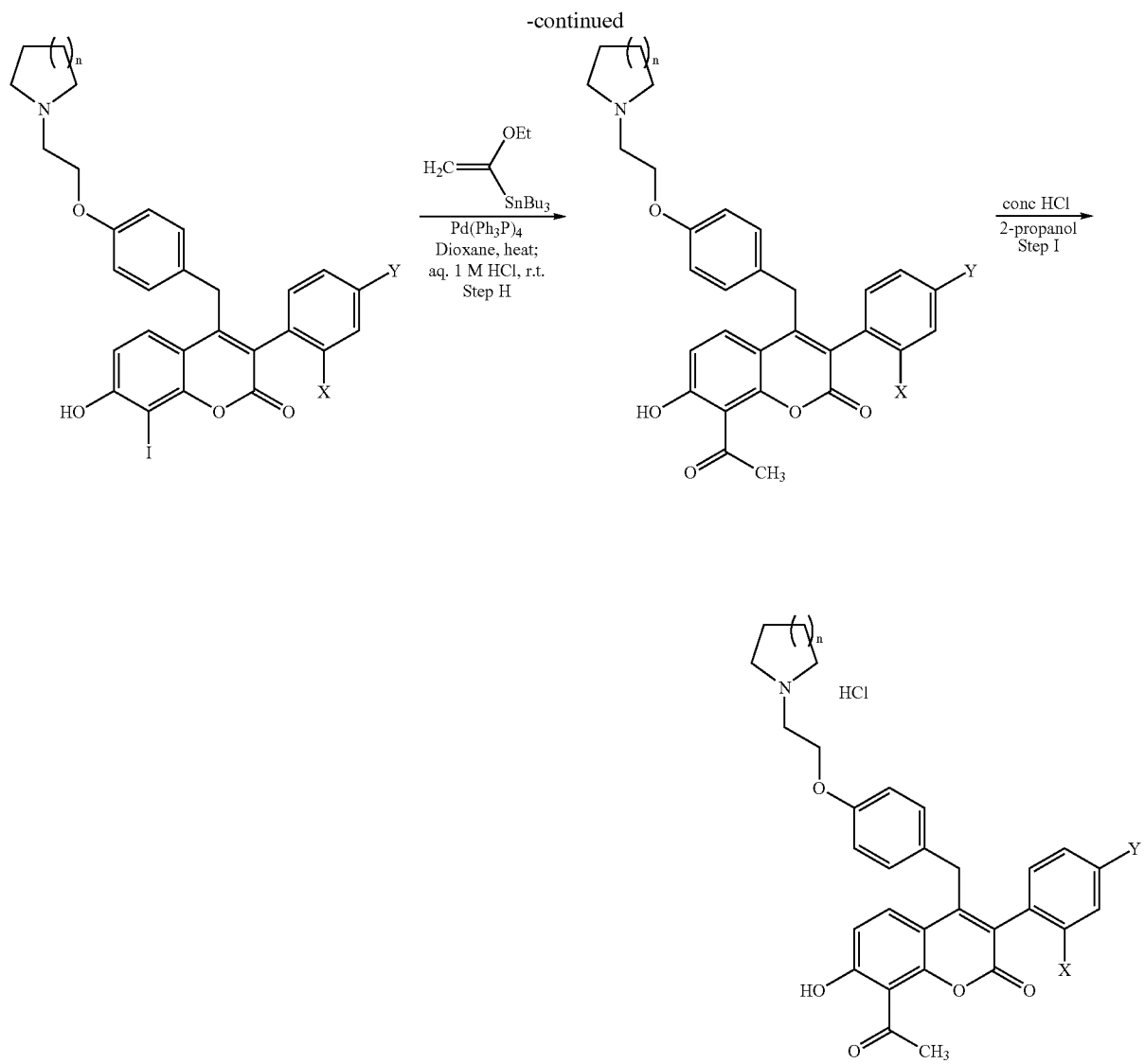
Illustrative examples of steps A–G in Scheme 2, above, are set forth in Example 3, below. Illustrative examples of steps H and I in Scheme 2, above, are set forth in Example 4, below.
Scheme 3:
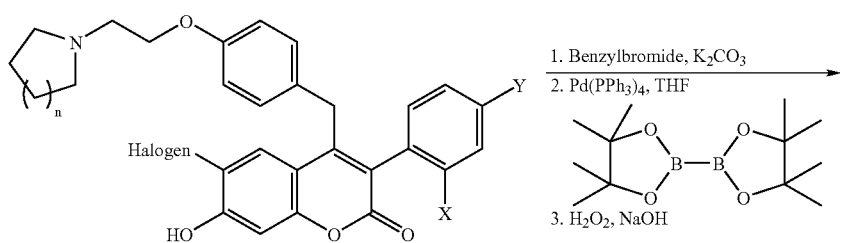

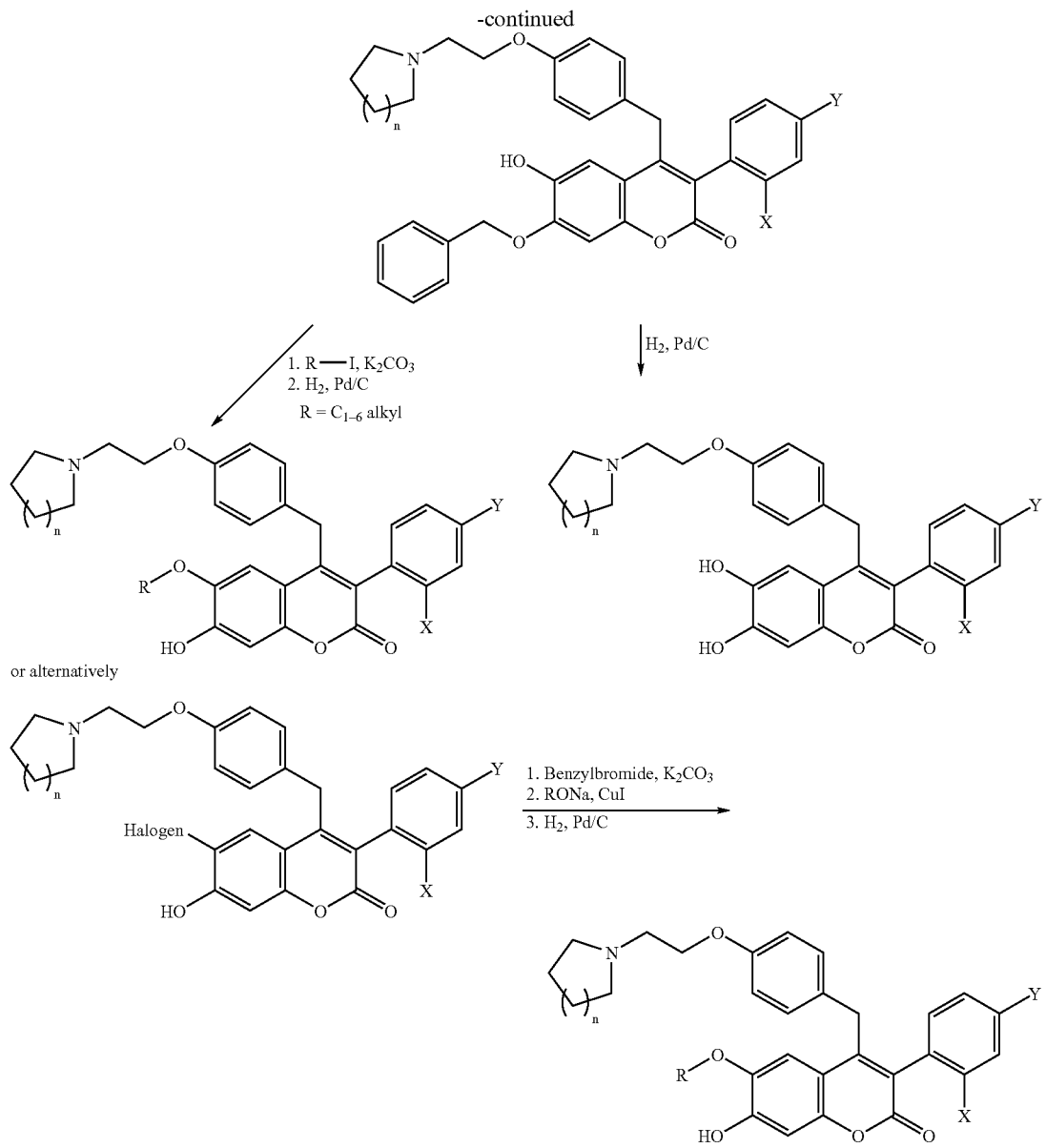
The starting material in Scheme 3 can be prepared as described in Example 9, below.
Scheme 4:
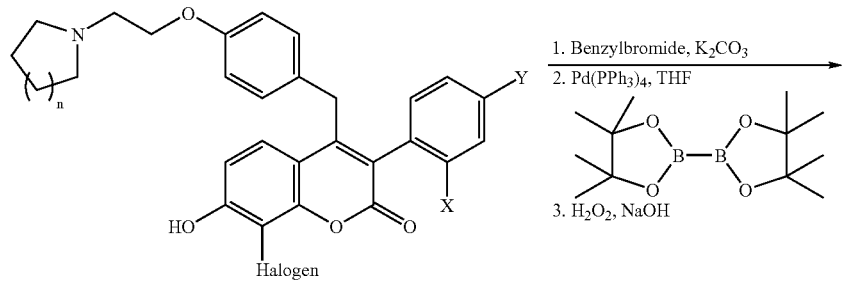

-continued
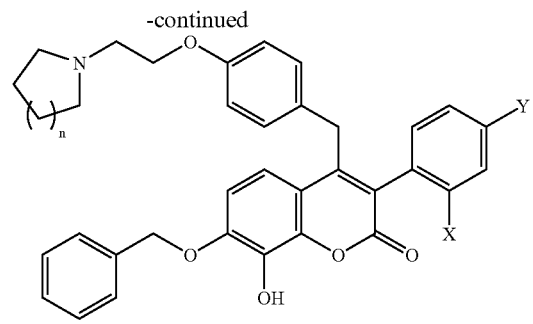
1. R—I, K$_2$CO$_3$
2. H$_2$, Pd/C
R = C$_{1-6}$ alkyl
H$_2$, Pd/C
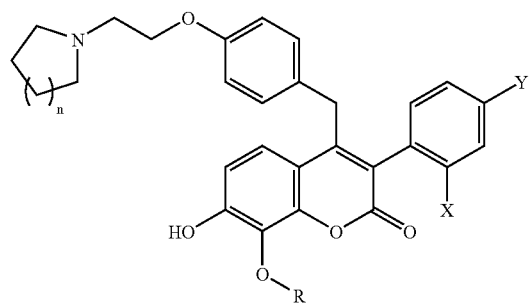
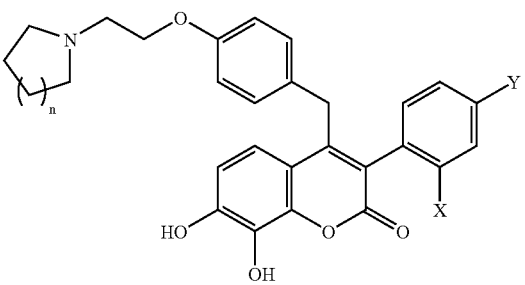
or alternatively
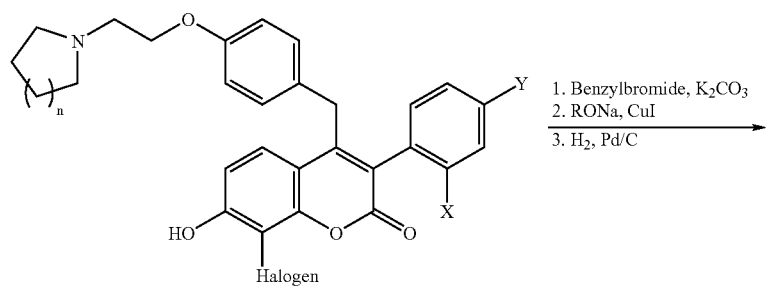
1. Benzylbromide, K$_2$CO$_3$
2. RONa, CuI
3. H$_2$, Pd/C
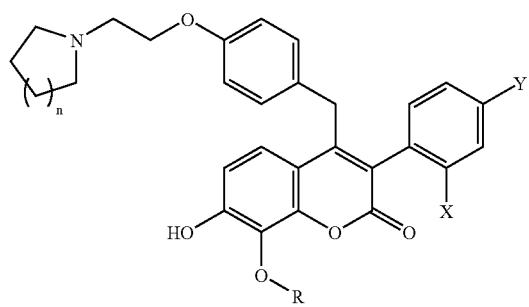
The starting material in Scheme 4 can be prepared as shown in Scheme 2, above.

Scheme 5:
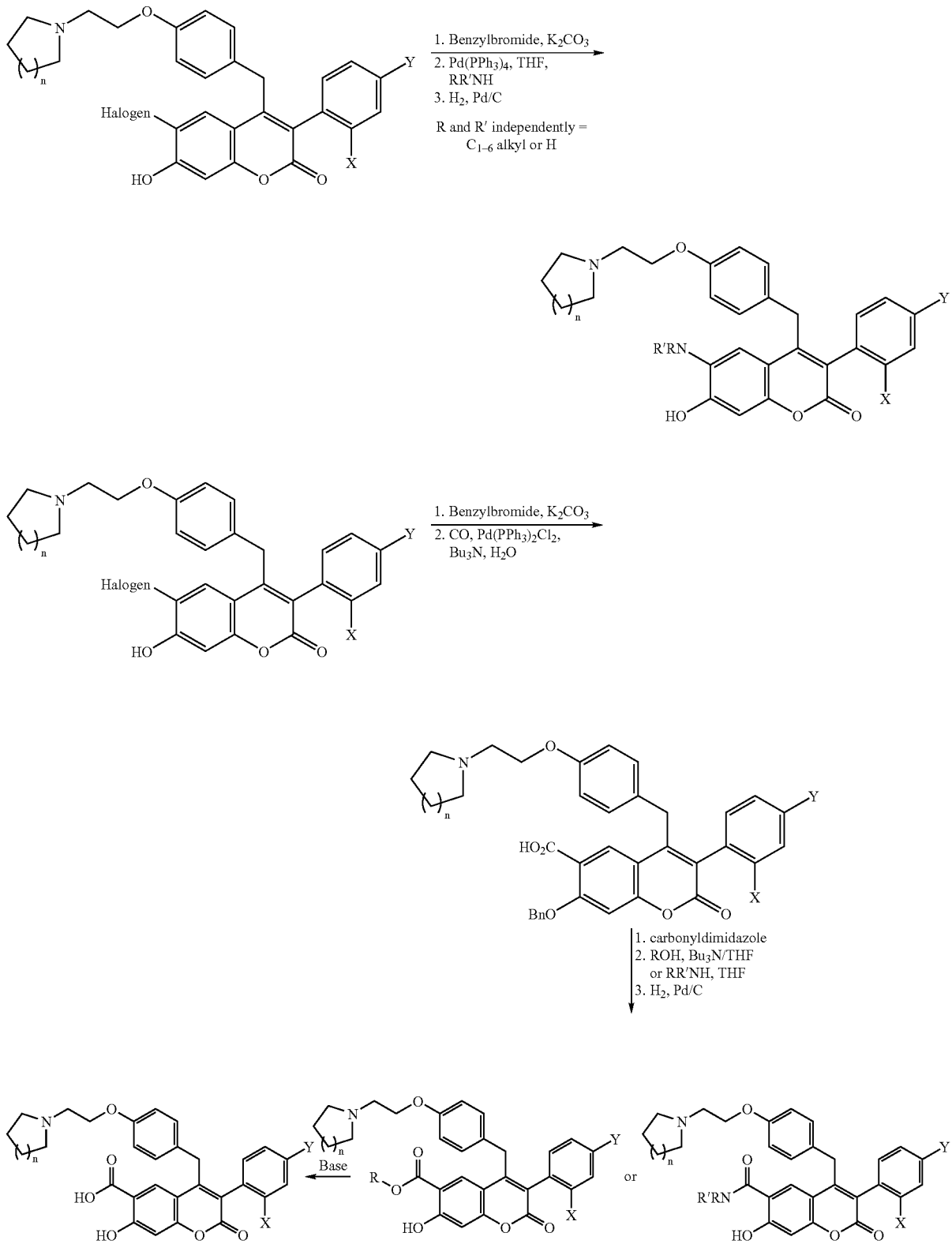
The starting material in Scheme 5 can be prepared as described in Example 9, below.

Scheme 6:
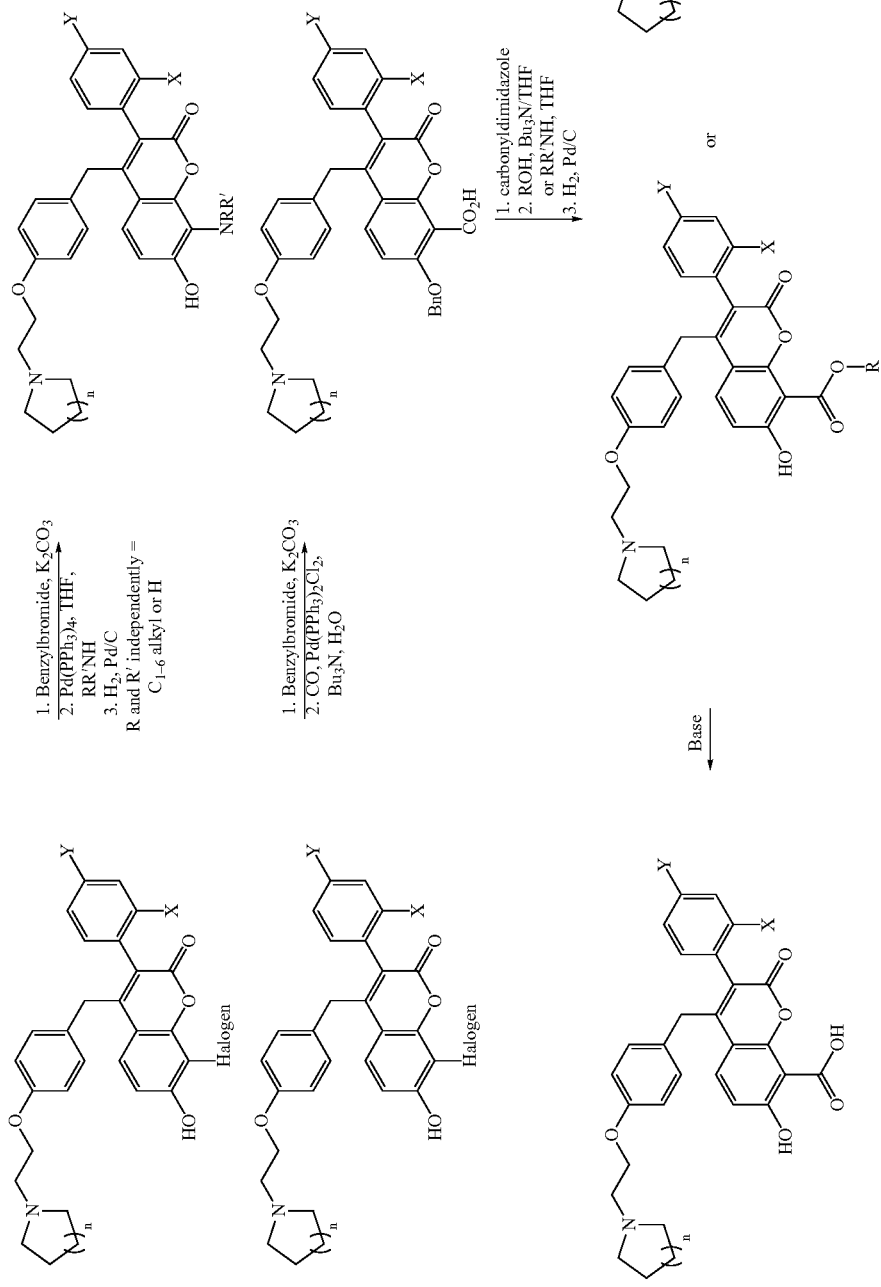

The starting material in Scheme 6 can be prepared as shown in Scheme 2, above.

Scheme 7:

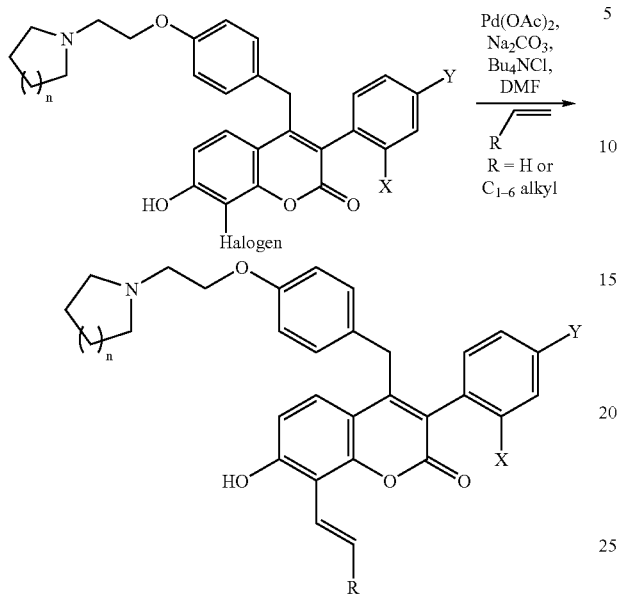

The starting material in Scheme 7 can be prepared as shown in Scheme 2, above.

Scheme 8:

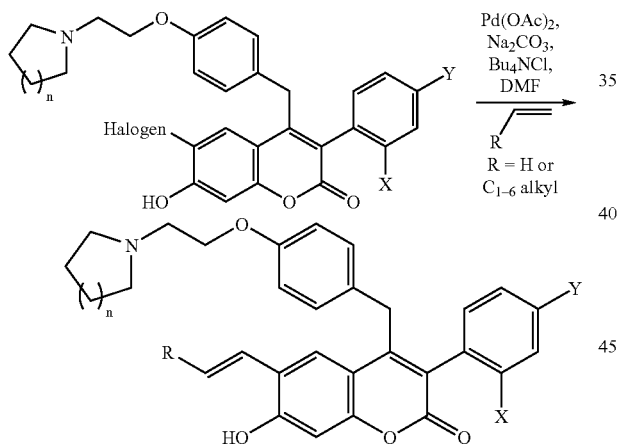

The starting material in Scheme 8 can be prepared as described in Example 9, below.

Scheme 9:

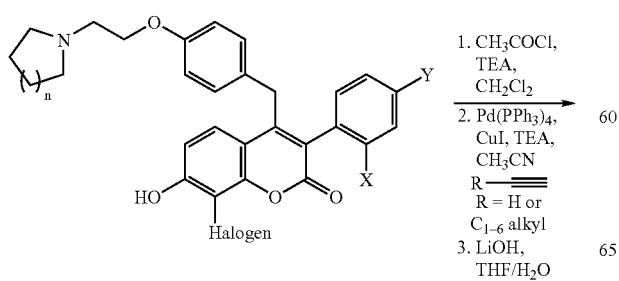

-continued

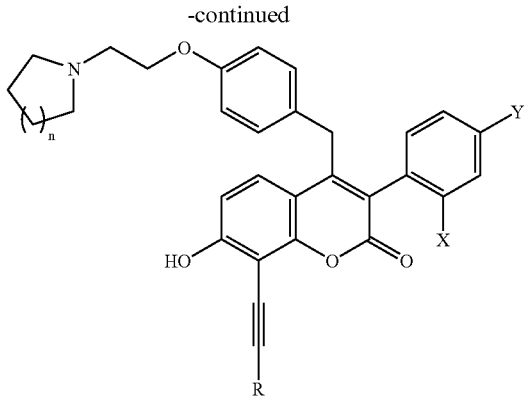

The starting material in Scheme 9 can be prepared as shown in Scheme 2, above.

Scheme 10:

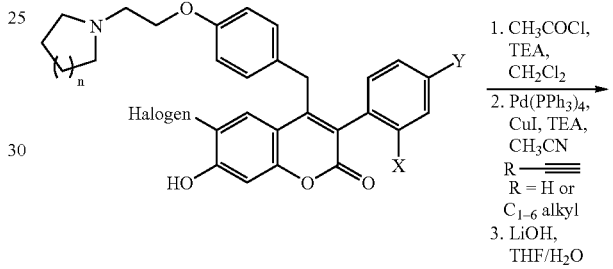

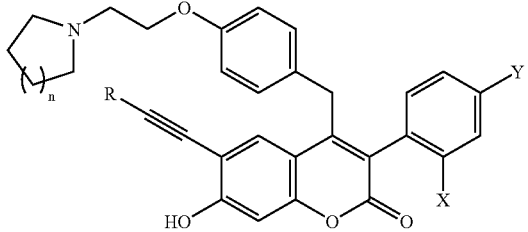

The starting material in Scheme 10 can be prepared as described in Example 9, below.

Scheme 11:

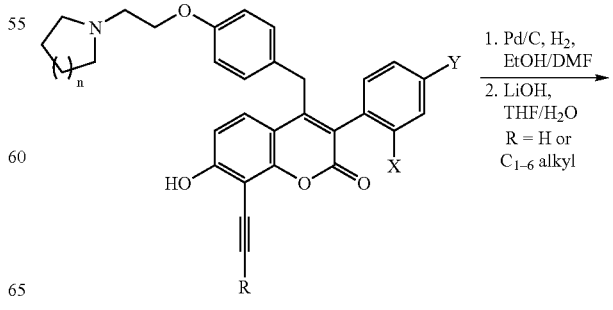

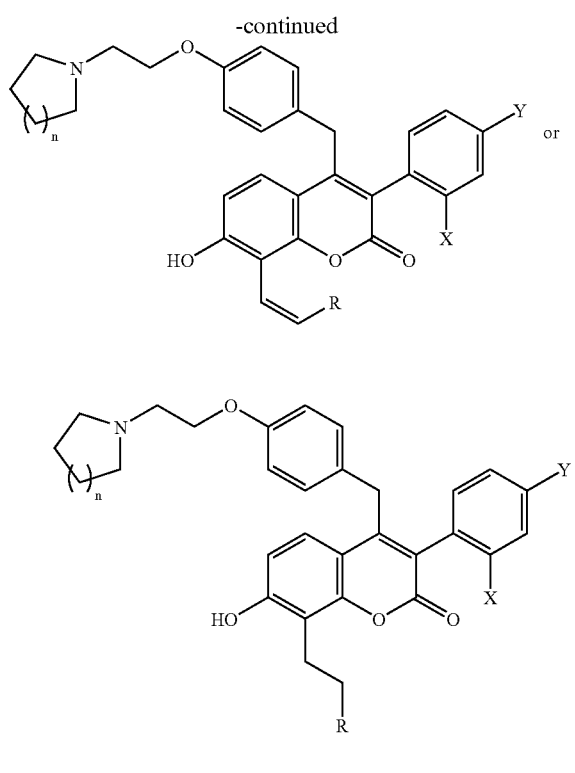
The starting material in Scheme 11 can be prepared as shown in Scheme 9, above.
Scheme 12:
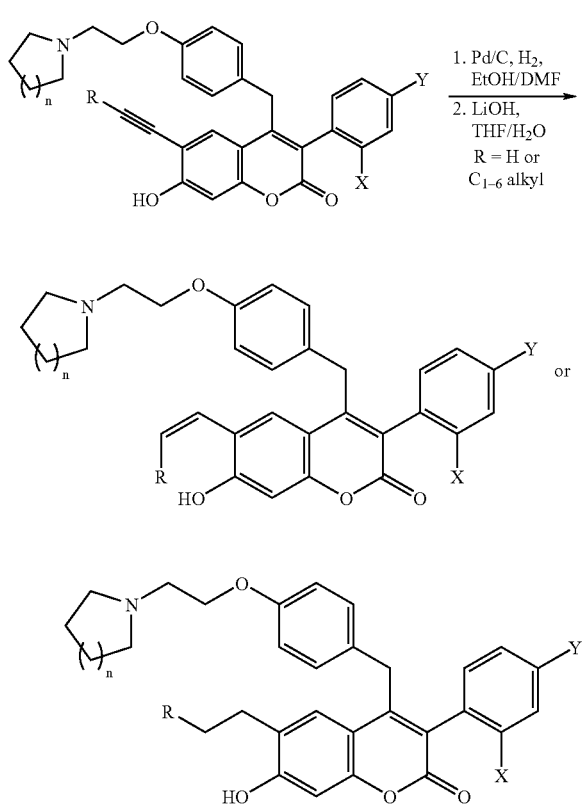
The starting material in Scheme 12 can be prepared as shown in Scheme 10, above.
Scheme 13:
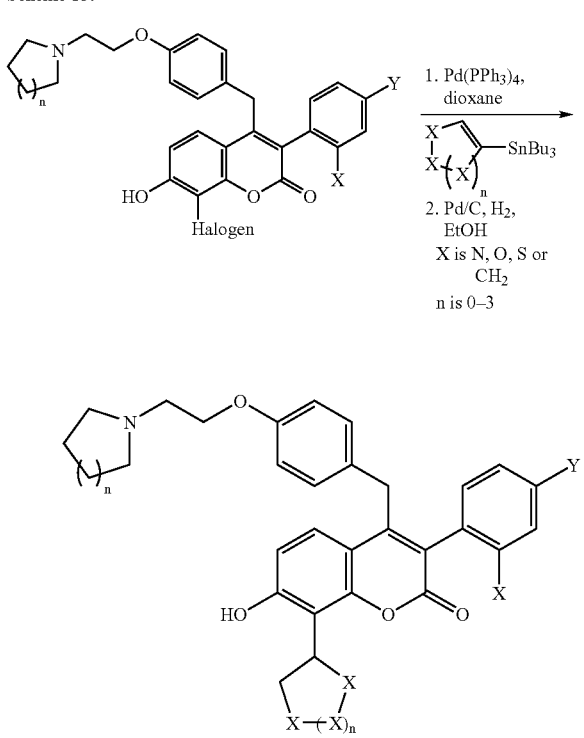
The starting material in Scheme 13 can be prepared as shown in Scheme 2, above.
Scheme 14:
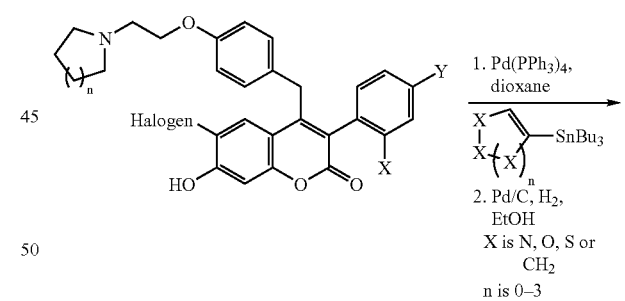
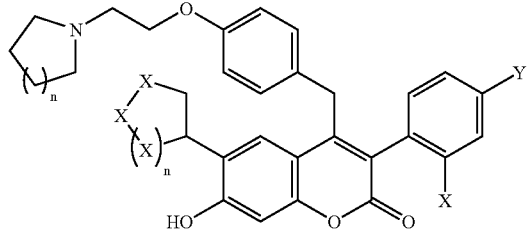
The starting material in Scheme 14 can be prepared as described in Example 9, below.

Scheme 15:

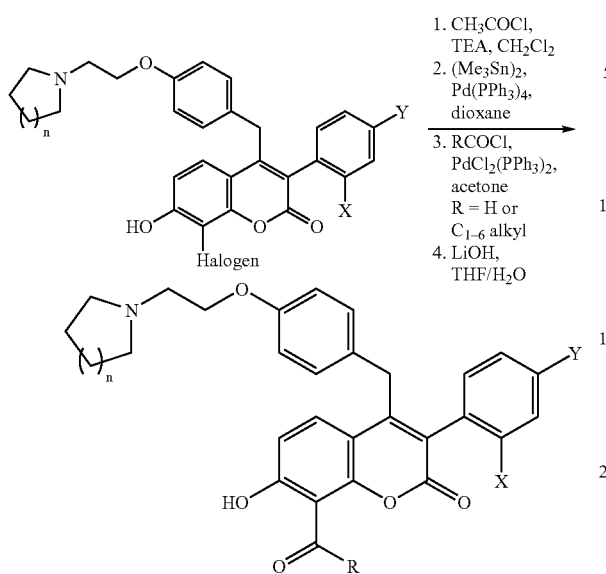

The starting material in Scheme 15 can be prepared as shown in Scheme 2, above.

Scheme 16:

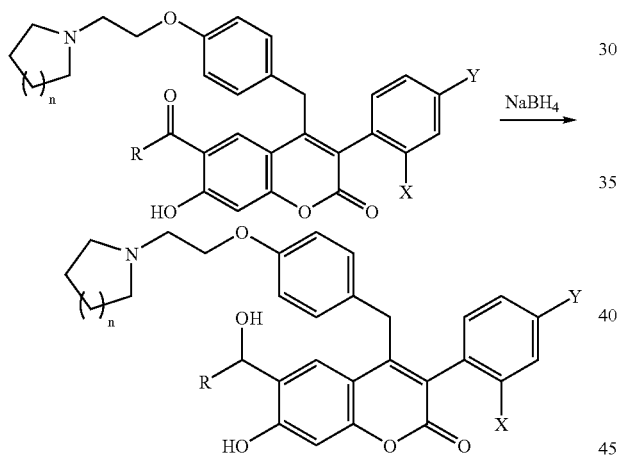

The starting material in Scheme 16 can be obtained by performing Step H shown in Scheme 2, above, on material obtained as described in Example 9, below. A solution of the corresponding 6-acetyl-7-hydroxychromen-2-one in THF/MeOH is treated with NaBH$_4$ at 0° C. Following complete reaction the desired product is isolated following purification of the crude reaction mixture.

Scheme 17:

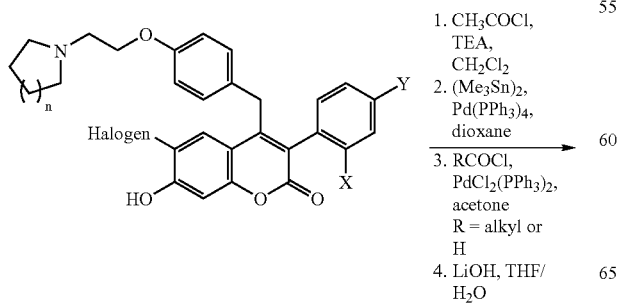

-continued

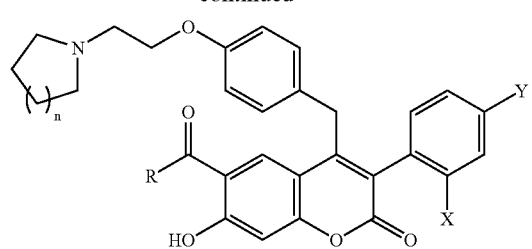

The starting material in Scheme 17 can be prepared as described in Example 9, below.

Scheme 18:

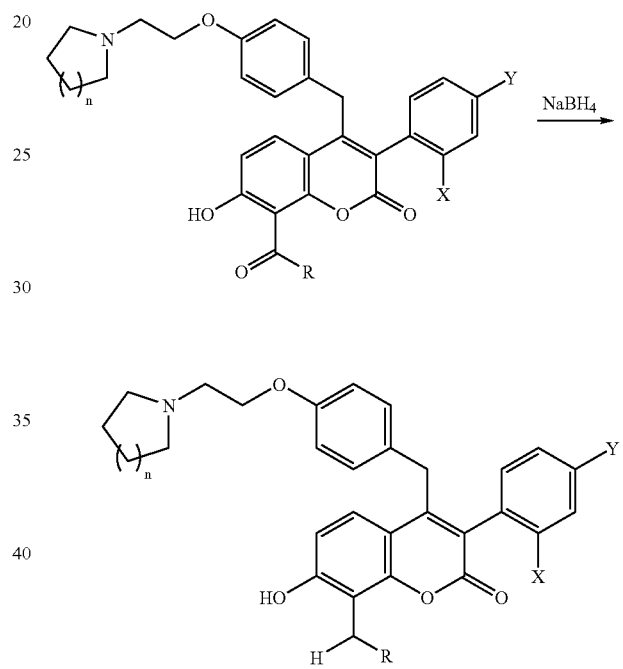

The starting material in Scheme 18 can be prepared as shown in Scheme 15, above. A solution of the corresponding 8-acetyl-7-hydroxychromen-2-one in THF/MeOH is treated with NaBH$_4$ at 0° C. Following complete reaction the desired product is isolated following purification of the crude reaction mixture.

Scheme 19:

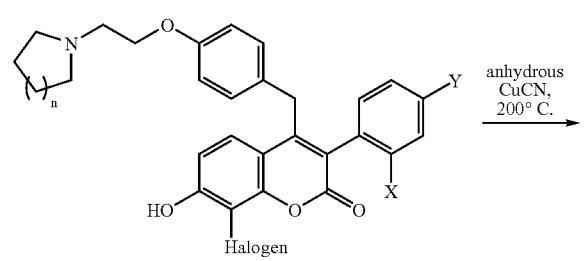

-continued
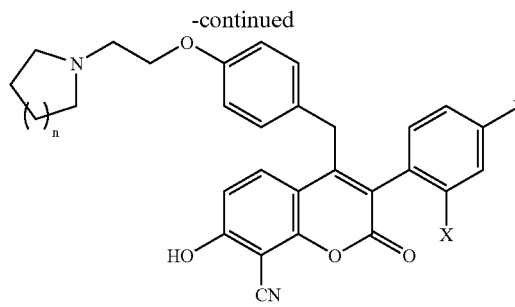
The starting material in Scheme 19 can be prepared as shown in Scheme 2, above.
Scheme 20:
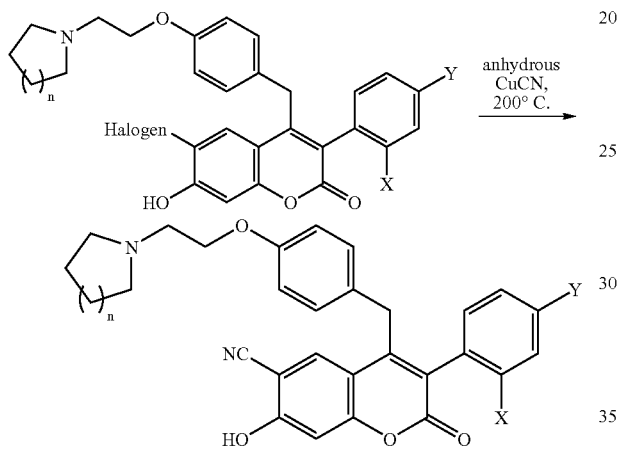
The starting material in Scheme 20 can be prepared as described in Example 9, below.
Scheme 21:
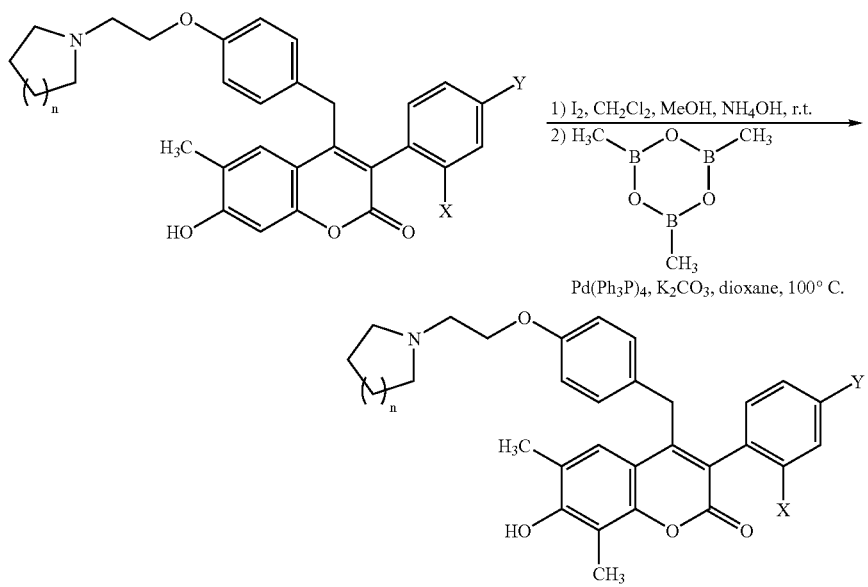
The starting material in Scheme 21 can be prepared as shown in Scheme 1, above.
Scheme 22:
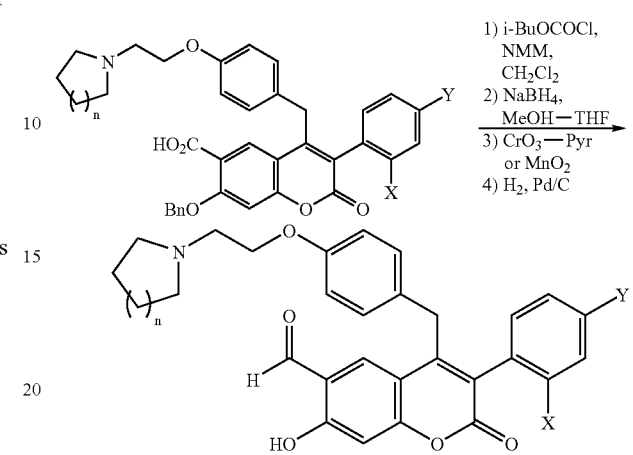
The starting material in Scheme 22 can be prepared as shown in Scheme 5, above.
Scheme 23:
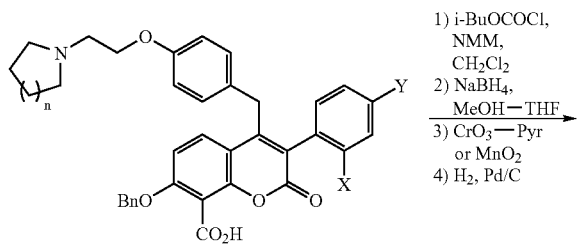

-continued

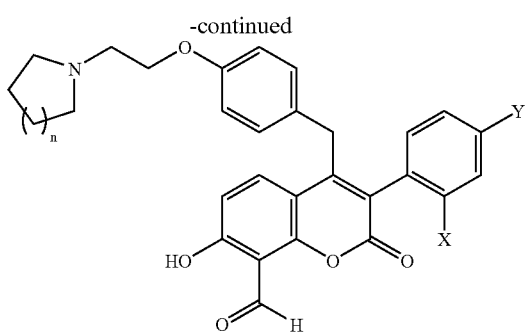

The starting material in Scheme 23 can be prepared as shown in Scheme 6, above.

In one embodiment, the invention relates to methods for making Benzopyranone Compounds, comprising demethylating a compound of formula (II):

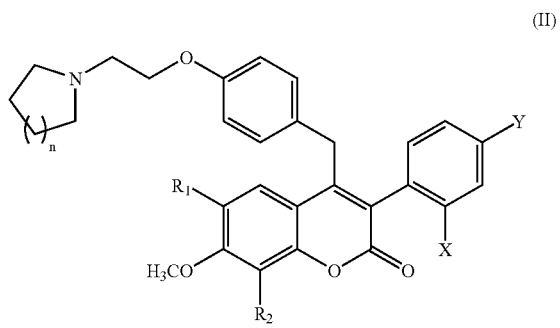

or a pharmaceutically acceptable salt thereof, wherein $R_1$, $R_2$, X, Y and n are as described above for the Benzopyranone Compounds.

The demethylation of compounds of formula (II) can be achieved using any method known in the art useful for the demethylation of phenolic methyl ethers. Examples of such methods can be found in Greene, T. W., *Protective Groups in Organic Synthesis*, 88–92 (1981), which is incorporated herein by reference in its entirety. In one embodiment, demethylation proceeds by a method comprising contacting a compound of formula (II) with about 1.0 to about 50.0 molar equivalents of a demethylating agent such as iodotrimethylsilane, pyridine hydrochloride, hydrobromic acid ("HBr"), hydrochloric acid, hydroiodic acid, $BBr_3$, a Grignard reagent (e.g., RMgX, wherein which R is a hydrocarbon radical such as $CH_3$, $C_2H_5$, $C_6H_5$, and the like; and X is a halogen atom, such as chlorine, bromine, or iodine), a Lewis acid (e.g., such as $AlBr_3$, $BF_3$, $BCl_3$, $B(CH)_3$, $Zn(OH)_2$, AgCl and the like) or a nucleophile such as ethanethiol. In one embodiment, the demethylating agent is aqueous HBr, which can be used in the presence of acetic acid. In another embodiment, demethylation is achieved by heating a compound of formula (II) or a pharmaceutically acceptable salt thereof in the presence of the demethylating agent, optionally in the presence of a solvent, including a carboxylic acid, at a temperature of about room temperature to about 200° C., in one embodiment at a temperature of about 100° C. to about 160° C., for 15 minutes to about 24 hours. In one embodiment, the demethylation reaction vessel is sealed, for example a sealed tube, to prevent solvent evaporation, particularly where the boiling point of the solvent is lower than the temperature of the demethylation reaction. The acid salt of the Benzopyranone Compounds can be obtained by isolating the salt directly from the demethylation reaction where the demethylating agent is, for example, hydrobromic acid, hydrochloric acid or hydroiodic acid. The free-base form is available upon washing the acid salt with an appropriate base such as sodium hydroxide and isolating the free-base compound.

The Benzopyranone Compounds can exist in the form of a pharmaceutically acceptable salt. The pharmaceutically acceptable acid salts can be formed by treating the free-base form of a Benzopyranone Compound with an acid. Suitable organic acids include maleic, fumaric, benzoic, ascorbic, succinic, methanesulfonic, benzenesulfonic, toluenesulfonic, acetic, oxalic, trifluoroacetic, propionic, tartaric, salicylic, citric, gluconic, lactic, mandelic, cinnamic, aspartic, stearic, palmitic, formic, glycolic, glutamic, and benzenesulfonic acids. Suitable inorganic acids include hydrochloric, hydrobromic, sulfuric, phosphoric, and nitric acids. Additional salts include chloride, bromide, iodide, bisulfate, acid phosphate, isonicotinate, lactate, acid citrate, oleate, tannate, pantothenate, bitartrate, gentisinate, gluconate, glucaronate, saccharate, ethanesulfonate, p-toluenesulfonate, and pamoate (i.e., 1,1'-methylene-bis-(2-hydroxy-3-naphthoate)) salts. The term "pharmaceutically acceptable salt" is intended to encompass any and all acceptable salt forms.

Pharmaceutically acceptable salts can be formed by conventional and known techniques, such as by reacting a Benzopyranone Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Benzopyranone Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

4.4 Methods of Use

In one embodiment, the invention relates to methods for treating or preventing a bone-resorbing disease, comprising administering an effective amount of a Benzopyranone Compound to a patient in need of the treating or preventing. Although not intending to be limited by the following theory, particularly in the context of bone-resorbing diseases, it is believed that the Benzopyranone Compounds function by blocking cytokine production and/or by inhibiting formation of osteoclasts. Particular bone-resorbing diseases that the Benzopyranone Compounds are useful for treating or preventing include, but are not limited to, osteoporosis, metastatic bone cancer, hypercalcemia, osteolytic lesions with orthopedic implants, Paget's disease, and bone loss associated with hyperparathyroidism.

In another embodiment, the invention relates to methods for treating or preventing a neoplastic disease, comprising administering an effective amount of a Benzopyranone Compound to a patient in need of the treating or preventing. In one embodiment, the neoplastic disease is cancer. In a particular embodiment, the cancer is a cancer of the head and neck, eye, skin, mouth, throat, esophagus, chest, bone, blood, lung, colon, sigmoid, rectum, stomach, prostate, breast, ovaries, uterine, kidney, liver, pancreas, brain, intestine, heart or adrenals. In another embodiment, the cancer is endometrial cancer, multiple myeloma, renal cell carcinoma or cervical carcinoma. The Benzopyranone Compounds are particularly useful for treating breast cancer, uterine cancer and ovarian cancer.

Still further cancers that the Benzopyranone Compounds are useful for treating or preventing include, but are not limited to, solid tumors, sarcomas, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, blood-borne tumors, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma.

In another embodiment, the invention relates to methods for treating or preventing arthritis, comprising administering an effective amount of a Benzopyranone Compound to a patient in need of the treating or preventing. In one embodiment, the arthritis is adjuvant-, collagen-, bacterial- or antigen-induced arthritis. In another embodiment, the arthritis is rheumatoid arthritis.

In another embodiment, the invention relates to methods for treating or preventing a disease exacerbated by the presence of estrogen, comprising administering an effective amount of a Benzopyranone Compound to a patient in need of the treating or preventing. In one embodiment, the disease exacerbated by the presence of estrogen is breast cancer, ovarian cancer or uterine cancer. In one embodiment, the estrogen is endogenous. In another embodiment, the estrogen is exogenous.

In another embodiment, the invention relates to methods for treating or preventing a disease improved by the presence of estrogen, comprising administering an effective amount of a Benzopyranone Compound to a patient in need of the treating or preventing. In one embodiment, the disease improved by the presence of estrogen in a patient is a bone-resorbing disease. In one embodiment, the disease improved by the presence of estrogen in a patient is osteoporosis, metastatic bone cancer, hypercalcemia, osteolytic lesions with orthopedic implants, Paget's disease, and bone loss associated with hyperparathyroidism. In one embodiment, the estrogen is endogenous. In another embodiment, the estrogen is exogenous.

In another embodiment, the invention relates to methods for treating or preventing endometriosis, hypercholesterolemia, prostatic hypertrophy, prostatic carcinoma, obesity, hot flashes, a skin effect (such as dry skin, wrinkling, thinning or loss of elasticity), mood swings, memory loss, a menopausal syndrome, hair loss (alopecia), type-II diabetes, Alzheimer's disease, urinary incontinence, a GI tract condition (such as Crohn's disease or irritable bowel syndrome), vascular protection after injury, a CNS effect (such as hot flashes or memory loss), acne or cataracts, comprising administering an effective amount of a Benzopyranone Compound to a patient in need of the treating or preventing. Without being bound by any particular theory, Applicants believe that the above conditions are improved by the presence of estrogen.

In another embodiment, the invention relates to methods for treating or preventing a cardiovascular disease, hirsutism, multiple myeloma or lymphoma, comprising administering an effective amount of a Benzopyranone Compound to a patient in need of the treating or preventing. Without being bound by any particular theory, Applicants believe that the above conditions are exacerbated by the presence of estrogen.

In another embodiment, the invention relates to methods for preventing spermatogenesis, comprising administering an effective amount of a Benzopyranone Compound to a patient in need of the preventing.

In another embodiment, the invention relates to methods for preventing an adverse reproductive effect (such as a birth defect, miscarriage or spontaneous abortion) associated with exposure to an environmental chemical or a natural hormonal imbalance, comprising administering an effective amount of a Benzopyranone Compound to a patient in need of the preventing.

In another embodiment, the Benzopyranone Compounds are useful for oral contraception; prevention of threatened or habitual abortion; relief of dysmenorrhea; relief of dysfunctional uterine bleeding; relief of endometriosis; an aid in ovarian development; diminution of excessive growth of body hair in women (hirsutism); prevention or treatment of atherosclerosis; and suppression of post-partum lactation. The Benzopyranone Compounds can also have a beneficial effect on plasma lipid levels and as such are useful for treating and preventing hypercholesterolemia.

In another embodiment, the invention relates to methods for activating the function of ER in a bone cell, comprising contacting a bone cell capable of expressing ER with an effective amount of a Benzopyranone Compound. Activating the function of ER in a bone cell is useful for treating or preventing osteoporosis.

In another embodiment, the invention relates to methods for inhibiting the function of ER in a cancer cell, comprising contacting a cancer cell capable of expressing ER with an effective amount of a Benzopyranone Compound. In one embodiment, the cancer cell is a breast cancer cell, an ovarian cancer cell, an endometrial cancer cell, a uterine cancer cell, a prostate cancer cell or a hypothalamus cancer cell. Inhibiting the function of ER in a cancer cell is useful for inhibiting the growth of the cell, and, accordingly, for treating or preventing cancer. In one embodiment, the breast cancer cell is MCF-7. In one embodiment, the ovarian cancer cell is BG-1.

In another embodiment, the invention relates to methods for inhibiting the expression of IL-6 in a cell, comprising contacting a cell capable of expressing ER and IL-6 with an effective amount of a Benzopyranone Compound. In one embodiment, the cell that expresses ER and IL-6 is a bone cell. In another embodiment, the cell that expresses ER and IL-6 is a human U-2 OS osteosarcoma cell stably transfected with human ER-β. Inhibiting the expression of IL-6 in a cell in vivo is useful for the treatment of a bone-loss disease or bone cancer. In one embodiment, the bone-loss disease is osteoporosis. Inhibiting the expression of IL-6 in a cell in vitro is useful in a biological activity screening assay (e.g., as a standard) for the screening of a Benzopyranone Compound that inhibits the expression of IL-6.

In another embodiment, the invention relates to methods for inhibiting growth of a neoplastic cell, comprising contacting a neoplastic cell capable of expressing ER with an effective amount of a Benzopyranone Compound. In one embodiment, the neoplastic cell capable of expressing ER is a cancer cell. Examples of cancer or neoplastic cells capable of expressing ER include, but are not limited to, breast cells, ovarian cells, endometrial cells, uterine cells, prostate cells and hypothalamus cells. Inhibiting the proliferation of such cancer or neoplastic cells in vivo is useful for the treatment or prevention of cancer. Inhibiting the proliferation of such cancer or neoplastic cells in vitro is useful in a biological activity screening assay (e.g., as a standard) for anti-cancer or anti-neoplastic agents or in a diagnostic assay.

4.5 Other Therapeutic Agents

In certain embodiments, the methods of the present invention further comprise the administration of an effective amount of another therapeutic agent. Examples of other therapeutic agents include, but are not limited to, agents useful for: treating or preventing a bone-resorbing disease, a neoplastic disease, arthritis, a disease exacerbated by the presence of estrogen or a disease improved by the presence of estrogen; activating the function of ER in a bone cell; inhibiting the function of ER in a cancer cell; inhibiting the expression of IL-6 in a cell; and inhibiting the growth of a neoplastic cell. The other therapeutic agent can be administered before, after or concurrently with the Benzopyranone Compound. In these embodiments, the time at which the Benzopyranone Compound exerts its therapeutic effect on the patient overlaps with the time at which the other therapeutic agent exerts its therapeutic effect on the patient.

In a further embodiment, the other therapeutic agent is useful for the treatment or prevention of a disease improved by the presence of estrogen. Other therapeutic agents that are useful for the treatment or prevention of a disease improved by the presence of estrogen include, but are not limited to, tamoxifen, raloxifene, medroxyprogesterone, danizol and gestrinone.

In one embodiment, the other therapeutic agent is useful for the treatment or prevention of a bone-loss disease (e.g., osteoporosis). Other therapeutic agents useful for the treatment or prevention of a bone-loss disease include, but are not limited to, cathepsin K inhibitors (e.g., a pro-peptide of cathepsin K), bisphosphonates (e.g., eitodronate, pamidronate, alendronate, risedronate, zolendronate, ibandronate, clodronate or tiludronate), parathyroid hormone ("PTH") or fragments thereof, compounds that release endogenous PTH (e.g., a PTH releasing hormone) and calcitonin or fragments thereof.

In another embodiment, the other therapeutic agent is useful for the treatment or prevention of a neoplastic disease. In one embodiment, the other therapeutic agent is useful for the treatment or prevention of cancer (e.g., cancer of the breast, ovary, uterine, prostate or hypothalamus). Other therapeutic agents useful for the treatment or prevention of cancer or a neoplastic disease include, but are not limited to, alkylating agents (e.g., nitrosoureas), an anti-metabolite (e.g., methotrexate or hydroxyurea), etoposides, campathecins, bleomycin, doxorubicin, daunorubicin, colchicine, irinotecan, camptothecin, cyclophosphamide, 5-fluorouracil, cisplatinum, carboplatin, methotrexate, trimetrexate, erbitux, thalidomide, taxol, a vinca alkaloid (e.g., vinblastine or vincristine) or a microtubule stabilizer (e.g., an epothilone).

Further illustrative examples of therapeutic agents useful for the treatment or prevention of cancer include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; ImiDs; interleukin II (including recombinant interleukin II, or rIL2), interferon-2a; interferon alpha-2b; interferon alpha-n1; interferon alpha-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; SelCid; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; temozolomide; temodar; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other therapeutic agents useful for the treatment or prevention of cancer include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); cell-cycle inhibitors (e.g., flavopiridol A, tryprostatin B, p19ink4D); cyclin-dependent kinase inhibitors (e.g., roscovitine, olomucine and purine analogs); MAP kinase inhibitors (CNI-1493); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; retinoic acid (e.g., 9-cis RA); histone deacetylase inhibitors (e.g., sodium butyrate, suberoylanilide hydroxamic acid); TRAIL; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

4.6 Pharmaceutical Compositions and Routes of Administration

The Benzopyranone Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Benzopyranone Compounds in the pharmaceutical composition may be at a level that will exercise the desired effect; for example, about 0.005 mg/kg of a patient's body weight to about 10 mg/kg of a patient's body weight in unit dosage for both oral and parenteral administration.

The Benzopyranone Compounds can be usually administered one to four times a day with a unit dosage of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day.

The dose of a Benzopyranone Compound to be administered to a patient is rather widely variable and can be subject to the judgment of a health-care practitioner. The general range of effective administration rates of a Benzopyranone Compound is from about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. Of course, it is often practical to administer the daily dose of Benzopyranone Compound in portions, at various hours of the day. However, in any given case, the amount of the Benzopyranone Compound administered will depend on such factors as the solubility of the active component, the formulation used and the route of administration.

A Benzopyranone Compound can be administered orally for reasons of convenience. However, the Benzopyranone Compound may equally effectively be administered intradermally, intramuscularly, intraperitoneally, percutaneously, intravenously, subcutaneously, intranasally, epidurally, sublingually, intracerebrally, intravaginally, transdermally, rectally, by inhalation, or topically to the ears, nose, eyes, or skin. The preferred mode of administration is left to the discretion of the health-care practitioner, and can depend in-part upon the site of the medical condition.

The present invention also relates to compositions comprising an effective amount of a Benzopyranone Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepare from water-soluble salts, such as the hydrochloride salt. In general, all of the compositions are prepared according to known methods in pharmaceutical chemistry. Capsules can be prepared by mixing a Benzopyranone Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Benzopyranone Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Benzopyranone Compound can be delayed or prolonged by proper formulation. For example, a slowly soluble pellet of the Benzopyranone Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Benzopyranone Compound in oily or emulsified vehicles that allow it to disperse slowly in the serum.

5. EXAMPLES

The following Examples are presented by way of illustration, not limitation.

5.1 Example 1

Synthesis of 7-hydroxy-6-methyl-4-(4-(2-pyrrolidin-1-yl-ethoxy)-benzyl)-3-(4-trifluoromethylphenyl)-chromen-2-one A. 1-(2-Hydroxy-4-methoxyphenyl)-2-(4-hydroxyphenyl)-ethanone

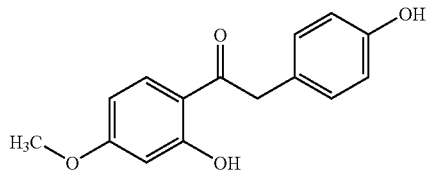

A suspension of 3-methoxyphenol (44.69 kg, 360 mol) and 4-hydroxyphenylacetic acid (68.5 kg, 450 mol) in 144 L of chlorobenzene was purged with nitrogen gas. Boron trifluoride diethyl etherate (177 L, 1440 mol) was added at 20 to 25° C. The suspension was heated to 80° C. and stirred for 4 to 5 h then cooled to 5 to 10° C. and stirred overnight.

The precipitated red/orange solid (undesired isomer) was filtered with $N_2$ pressure, and the filtrate was quenched by pouring it onto ice/$H_2O$. The resultant filter cake was washed with $CH_2Cl_2$, and the boron trifluoride etherate in the solution was quenched by the slow addition of 80% $Na_2CO_3$ (aq) until the pH of the aqueous solution reached 6 to 7. Gas evolution was observed and the desired product precipitated from solution forming an orange suspension. The orange suspension was stirred at 20° C. overnight and subsequently filtered. The resultant filter cake was washed with $H_2O$ and methyl t-butyl ether ("MTBE") and dried overnight to provide the desired product (38 kg, 42% yield, HPLC purity 95.1% a/a). $^1$H NMR (300 MHz, DMSO-$d_6$) 12.30 (s, 1H), 9.31 (s, 1H), 7.99 (d, 1H, J=9.1 Hz), 7.08 (d, 2H, J=8.4 Hz), 6.70, (d, 2H, J=8.4 Hz), 6.53 (dd, 1H, J=2.5, 9.1 Hz), 6.47 (d, 1H, J=2.5 Hz), 4.18 (s, 2H), 3.81 (s, 3H). MS (ESI) m/z 259 (M+H)$^+$.

B. 4-(4-Hydroxybenzyl)-7-methoxy-3-(4-trifluoromethyl-phenyl)-chromen-2-one

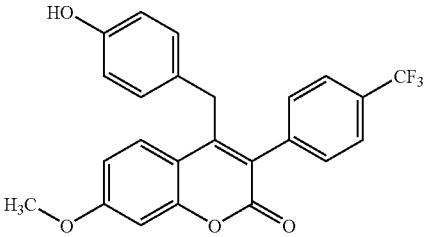

A solution of 4-trifluoromethylphenylacetic acid (15.2 g, 74.45 mmol) in 120 mL of DMF at 25° C. was treated with carbonyl diimidazole ("CDI") (13.2 g, 82 mmol) in several portions over 5 minutes. The reaction mixture was warmed to 40° C. for 10 minutes then cooled to room temperature. 1-(2-hydroxy-4-methoxyphenyl)-2-(4-hydroxyphenyl) ethan-1-one (9.81 g, 38 mmol), $K_2CO_3$ (15.7 g, 114 mmol), and DMAP (0.93 g, 7.6 mmol) were added, and the reaction mixture was warmed to 80° C. for 2 hours.

The resultant suspension was cooled to room temperature and 200 mL of water was added. The aqueous layer was extracted with $CH_2Cl_2$, and the organic layer was dried (MgSO$_4$) then concentrated under vacuum. The resulting solid was purified using flash chromatography ($CH_2Cl_2$: EtOAc) to provide the desired product (10.2 g, 63%).
$^1$H NMR (300 MHz, DMSO-$d_6$) 9.29 (s, 1H), 7.79 (d, 2H, J=8.7 Hz), 7.57 (d, 2H, J=8.7 Hz), 7.53 (d, 1H, J=8.5 Hz), 7.04 (d, 1H, J=2.3 Hz), 6.93 (d, 2H, J=8.9 Hz), 6.87 (dd, 1H, J=8.5, 2.3 Hz), 6.61 (d, 2H, J=8.9 Hz), 3.90 (s, 2H), 3.84 (s, 3H).
MS (ESI) m/z 427 (M+H)$^+$.

C. 2,2-Dimethyl-propionic acid 4-(7-methoxy-2-oxo-3-(4-trifluoromethyl-phenyl)-2H-chromen-4-ylmethyl)-phenyl ester

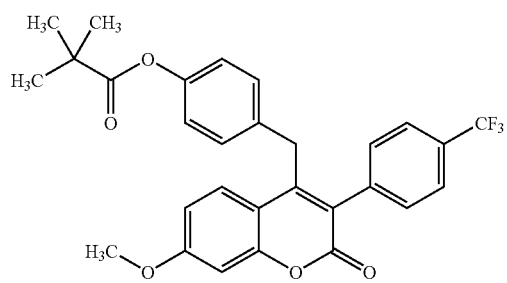

A mixture of 4-(4-hydroxybenzyl)-7-methoxy-3-(4-trifluoromethyl-phenyl)-chromen-2-one (800 mg, 1.88 mmol), pivaloyl chloride (577 µL, 4.69 mmol), imidazole (268 mg, 3.94 mmol) and DMAP (344 mg, 2.81 mmol) in DMF (10 mL) was stirred at room temperature for 18 h. Additional portions of imidazole (268 mg, 3.94 mmol), DMAP (344 mg, 2.81 mmol) and pivaloyl chloride (577 µL, 4.69 mmol) were added and stirring was continued for a further 20 h, for a total reaction time of 38 h. The solvent was removed in vacuo, the residue was dissolved in AcOEt and the organic layer was washed with H₂O. The aq layer was extracted with AcOEt (2×) and the combined organic layers were washed with brine, dried (MgSO₄) and the solvent was removed in vacuo. The resultant residue was purified using flash chromatography (silica gel, 5:1 hexanes:AcOEt) to provide the title compound as a white solid (820 mg, 86%). ¹H NMR (300 MHz, CDCl₃) δ 7.64 (d, J=8.0 Hz, 2H), 7.43–7.37 (m, 3H), 7.08–7.02 (m, 2H), 7.00–6.93 (m, 2H), 6.88 (d, J=2.5 Hz, 1H), 6.77 (dd, J=2.5, 8.8 Hz, 1H), 4.04 (s, 2H), 3.87 (s, 3H), 1.34 (s, 9H); MS (ESI) m/z 511.0 (M+H)⁺; HPLC t_R 7.58 min.

D. 2,2-Dimethyl-propionic acid 4-(6-bromo-7-methoxy-2-oxo-3-(4-trifluoromethyl-phenyl)-2H-chromen-4-ylmethyl)-phenyl ester

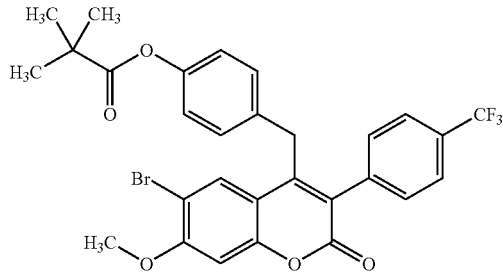

A mixture of 2,2-dimethyl-propionic acid 4-(7-methoxy-2-oxo-3-(4-trifluoromethyl-phenyl)-2H-chromen-4-ylmethyl)-phenyl ester from step C (820 mg, 1.61 mmol) and Br₂ (83 μL, 1.61 mmol) in AcOH (15 mL) was stirred at room temperature for 16 h. Another portion of Br₂ (80 μL, 1.55 mmol) was added, and stirring was continued for 6 h. The mixture was poured into H₂O, and the aqueous layer was extracted with CH₂Cl₂ (2×). The combined organic layers were washed with brine, dried (MgSO₄) and concentrated in vacuo. The residual orange solid was crystallized from CH₂Cl₂/hexane to afford the desired compound as a white solid (710 mg, 75%). ¹H NMR (300 MHz, CDCl₃) δ 7.67 (s, 1H), 7.65 (d, J=8.5 Hz, 2H), 7.38 (d, J=8.5 Hz, 2H), 7.07–6.94 (m, 4H), 6.89 (s, 1H), 4.01 (s, 2H), 3.98 (s, 3H), 1.35 (s, 9H); MS (ESI) m/z 588.8 (M+H)⁺; HPLC t_R 7.78 min.

E. 2,2-Dimethyl-propionic acid 4-(7-methoxy-6-methyl-2-oxo-3-(4-trifluoromethyl-phenyl)-2H-chromen-4-ylmethyl)-phenyl ester

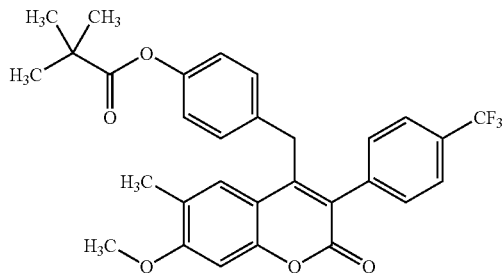

A mixture of 2,2-dimethyl-propionic acid 4-(6-bromo-7-methoxy-2-oxo-3-(4-trifluoromethyl-phenyl)-2H-chromen-4-ylmethyl)-phenyl ester (100 mg, 0.17 mmol), K₂CO₃ (70 mg, 0.51 mmol), trimethylboroxine (24 μL, 0.17 mmol) and Pd(Ph₃P)₄ (20 mg, 0.017 mmol) in anhydrous dioxane (2 mL) was stirred at reflux temperature for 2 h. After cooling to room temperature, the resultant suspension was filtered over Celite, and the solvent was removed in vacuo. The residue was recrystallized from CH₂Cl₂/hexane to afford the desired compound as a beige solid (72 mg, 82%) displaying. ¹H NMR (300 MHz, CDCl₃) δ 7.62 (d, J=8.0 Hz, 2H), 7.36 (d, J=8.0 Hz, 2H), 7.22 (d, J=0.9 Hz, 1H), 7.04 (d, J=8.8 Hz, 2H), 6.96 (d, J=8.8 Hz, 2H), 6.83 (s, 1H), 4.02 (s, 2H), 3.91 (s, 3H), 2.16 (s, 3H), 1.35 (s, 9H); MS (ESI) m/z 524.9 (M+H)⁺, HPLC t_R 7.81 min.

F. 4-(4-Hydroxybenzyl)-7-methoxy-6-methyl-3-(4-trifluoromethyl-phenyl)-chromen-2-one

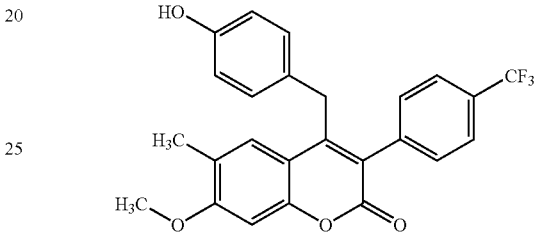

A mixture of 2,2-dimethyl-propionic acid 4-(7-methoxy-6-methyl-2-oxo-3-(4-trifluoromethyl-phenyl)-2H-chromen-4-ylmethyl)-phenyl ester (72 mg, 0.14 mmol) and LiOH·H₂O (23 mg, 0.55 mmol) in an 8:1 mixture of THF:H₂O (4.5 mL) was stirred at 30° C. for 4 h. THF was removed in vacuo and AcOEt was added. The pH of the aqueous layer was lowered to 5 by addition of aqueous 1N HCl. The layers were separated and the aqueous phase was extracted with AcOEt (2×). The combined organic layers were washed with brine, dried (MgSO₄) and concentrated. The residue was purified using flash chromatography (99:1 CH₂Cl₂:MeOH) to provide the desired compound as a beige solid (40 mg, 67%). ¹H NMR (300 MHz, CDCl₃) δ 7.62 (d, J=8.0 Hz, 2H), 7.38 (d, J=8.0 Hz, 2H), 7.25 (d, J=1.0 Hz, 1H), 6.92–6.86 (m, 2H), 6.82 (s, 1H), 6.75–6.69 (m, 2H), 3.95 (s, 2H), 3.90 (s, 3H), 2.16 (s, 3H); MS (ESI) m/z 440.9 (M+H)⁺; HPLC t_R 6.50 min.

G. 7-Methoxy-6-methyl-4-(4-(2-pyrrolidin-1-yl-ethoxy)-benzyl)-3-(4-trifluoromethyl-phenyl)-chromen-2-one

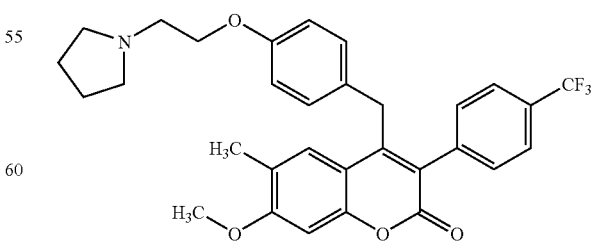

A mixture of 4-(4-hydroxybenzyl)-7-methoxy-6-methyl-3-(4-trifluoromethyl-phenyl)-chromen-2-one (50 mg, 0.113 mmol), K₂CO₃ (48 mg, 0.35 mmol) and 1-(2-chloroethyl)

pyrrolidine.HCl (24 mg, 0.14 mmol) in EtOH (1 mL) containing water (100 μL) was stirred at 55° C. for 5 h. The mixture was cooled to room temperature and was poured into CH$_2$Cl$_2$—H$_2$O. The layers were separated and the aqueous phase was extracted with CH$_2$Cl$_2$ (3×). The combined organic layers were dried (MgSO$_4$) and the solvent was removed in vacuo. The residue was purified using flash chromatography (silica gel, 40:1 CH$_2$Cl$_2$:MeOH) to provide the title compound as a beige solid (37 mg, 61%). MS (ESI) m/z 537.9 (M+H)$^+$; HPLC t$_R$ 5.22 min.

H. 7-Hydroxy-6-methyl-4-(4-(2-pyrrolidin-1-yl-ethoxy)-benzyl)-3-(4-trifluoromethyl-phenyl)-chromen-2-one

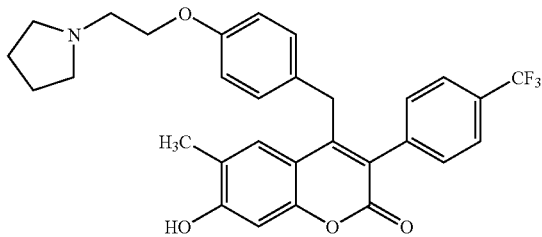

A solution of 7-methoxy-6-methyl-4-(4-(2-pyrrolidin-1-yl-ethoxy)-benzyl)-3-(4-trifluoromethyl-phenyl)-chromen-2-one (50 mg, 0.093 mmol) in 1:1 48% HBr:AcOH (3 μL) was heated at 130° C. for 7 h. The mixture was cooled to room temperature and poured into AcOEt/1 M NaOH. The layers were separated and the organic phase was washed with H$_2$O (2×) and brine and dried (MgSO$_4$). The solvent was removed in vacuo. The residue was purified using reverse phase HPLC, followed by extraction with AcOEt/NaHCO$_3$ to provide the desired compound as a yellow solid (25 mg, 52%). $^1$H NMR (300 MHz, CDCl$_3$) δ 7.60 (d, J=8.0 Hz, 2H), 7.32 (d, J=8.0 Hz, 2H), 7.21 (d, J=0.75 Hz, 1H), 6.86 (d, J=8.8 Hz, 2H), 6.72 (s, 1H), 6.62 (d, J=8.8 Hz, 2H), 4.14 (t, J=5.5 Hz, 2H), 3.92 (s, 2H), 3.13 (t, J=5.5 Hz, 2H), 2.97–2.85 (br s, 4H), 2.13 (s, 3H), 2.00–1.89 (m, 4H); MS (ESI) m/z 523.9 (M)$^+$; HPLC t$_R$ 5.07 min.

5.2 Example 2

Synthesis of 3-(2,4-dichlorophenyl)-7-hydroxy-6-methyl-4-(4-(2-pyrrolidin-1-yl-ethoxy)-benzyl)-chromen-2-one The synthesis of the above-titled compound was carried out according to the protocol of Example 1, except that 2,4-dichlorophenylacetic acid was used in place of 4-(trifluoromethyl)phenylacetic acid in step B.

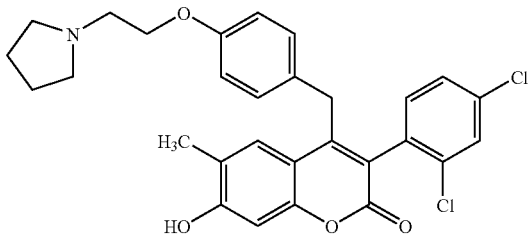

$^1$H NMR (300 MHz, DMSO) δ 10.8–10–4 (br s, 1H), 7.70 (d, J=2.0 Hz, 1H), 7.46 (dd, J=2.0, 8.0 Hz, 1H), 7.42 (s, 1H), 7.38 (d, J=8.5 Hz, 1H), 6.98 (d, J=8.8 Hz, 2H), 6.78 (s, 1H), 6.76 (d, J=8.8 Hz, 2H), 4.02 (d, J=15.5 Hz, 1H), 3.97 (t, J=6.0 Hz, 2H), 3.70 (d, J=15.5 Hz, 1H), 2.78 (t, J=6.0 Hz, 2H), 2.58–2.46 (m, 4H), 2.07 (s, 3H), 1.72–1.61 (m, 4H); MS (ESI) m/z 523.8 (M+H)$^+$; HPLC t$_R$ 5.14 min.

5.3 Example 3

Synthesis of 3-(2,4-dichlorophenyl)-7-hydroxy-8-methyl-4-(4-(2-pyrrolidin-1-yl-ethoxy)-benzyl)-chromen-2-one

A. 1-(2-Hydroxy-4-methoxyphenyl)-2-(4-hydroxyphenyl)-ethanone

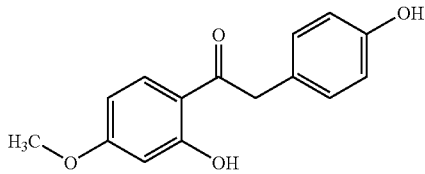

A suspension of 3-methoxyphenol (44.69 kg, 360 mol) and 4-hydroxyphenylacetic acid (68.5 kg, 450 mol) in 144 L of chlorobenzene was purged with nitrogen gas. Boron trifluoride diethyl etherate (177 L, 1440 mol) was added at 20 to 25° C. The resultant suspension was heated to 80° C., stirred for 4 to 5 h, cooled to 5 to 10° C. and stirred overnight.

The resultant red/orange solid (undesired isomer) precipitate was filtered with N$_2$ pressure and the filtrate was quenched by pouring it onto ice/H$_2$O. The filter cake containing the undesired isomer was washed with CH$_2$Cl$_2$, and the boron trifluoride etherate in the solution was quenched by the slow addition of 80% Na$_2$CO$_3$ (aq) until the pH of the aqueous solution reached 6 to 7. Gas evolution was observed, and the product precipitated from solution, forming and orange suspension. The orange suspension was stirred at 20° C. overnight and subsequently filtered. The resultant filter cake was washed with H$_2$O and MTBE and dried overnight to provide the desired product (38 kg, 42% yield, HPLC purity 95.1% a/a). $^1$H NMR (300 MHz, DMSO-d$_6$) 12.30 (s, 1H), 9.31 (s, 1H), 7.99 (d, 1H, J=9.1 Hz), 7.08 (d, 2H, J=8.4 Hz), 6.70, (d, 2H, J=8.4 Hz), 6.53 (dd, 1H, J=2.5, 9.1 Hz), 6.47 (d, 1H, J=2.5 Hz), 4.18 (s, 2H), 3.81 (s, 3H). MS (ESI) m/z 259 (M+H)$^+$.

B. 3-(2,4-Dichlorophenyl)-4-(4-hydroxybenzyl)-7-methoxy-chromen-2-one

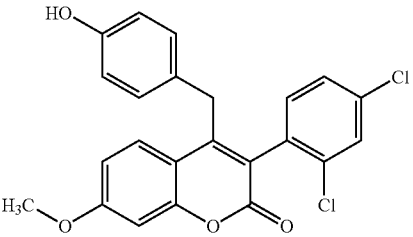

The above-titled compound was prepared using the method described above in Example 1B, except that except that 2,4-dichlorophenylacetic acid was used in place of 4-trifluoromethylphenylacetic acid. 20 grams ketone (77.5 mmol) and 31.6 grams acid (155 mmol) provided 27.52 grams product (83%). $^1$H NMR (300 MHz, DMSO-d$_6$) 9.26

(s, 1H), 7.58 (d, 1H, J=8.8 Hz), 7.50 (dd, 1H, J=1.9, 8.2 Hz), 7.45 (d, 1H, J=8.2 Hz), 7.06 (d, 1H, J=2.2 Hz), 6.90 (d, 3H, J=8.2 Hz), 6.59 (d, 2H, J=8.2 Hz), 3.98 (d, 1H, J=15.4 Hz), 3.85 (s, 3H), 3.69 (d, 1H, J=15.4 Hz). MS (ESI) m/z 428 (M+H)$^+$.

C. 4-(4-(2-Bromoethoxy)-benzyl)-3-(2,4-dichlorophenyl)-7-methoxy-chromen-2-one

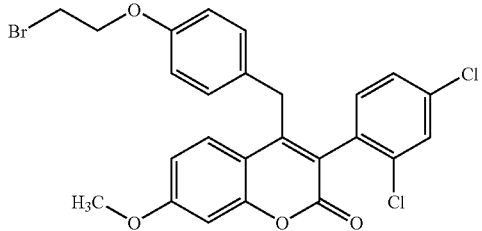

A mixture of 3-(2,4-dichlorophenyl)-4-(4-hydroxybenzyl)-7-methoxy-chromen-2-one (6.4 g, 15.0 mmol), 1,2-dibromoethane (12.9 mL, 149.8 mmol) and $K_2CO_3$ (4.14 g, 30 mmol) in acetone (65 mL) was stirred at reflux temperature for 20.5 h. An additional portion of $K_2CO_3$ (241.6 mg, 1.75 mmol) and 1,2-dibromoethane (3.2 mL, 37.5 mmol) was added at that time and once more 7.5 h later. Heating was continued for an additional 20 h, for a total reaction time of 48 h. The resultant mixture was cooled to room temperature and poured into $CH_2Cl_2/H_2O$. The layers were separated, and the aqueous phase was extracted with $CH_2Cl_2$ (2×). The combined organic layers were washed with brine (2×) and dried ($MgSO_4$), and the solvent was removed in vacuo. The resultant residue was purified using flash chromatography (300 g silica gel, 4.5:1:1→4:1:1→3:1:1 hexanes:$CH_2Cl_2$:AcOEt) to provide the title compound as a white solid (4.851 g, 61%) in addition to recovered starting material (2.054 g, 32%). $^1$H NMR (300 MHz, CDCl$_3$) δ 7.50 (d, J=2.0 Hz, 1H), 7.44 (d, J=9.0 Hz, 1H), 7.26 (dd, J=2.0, 8.0 Hz, 1H), 7.12 (d, J=8.0 Hz, 1H), 6.98–6.91 (m, 2H), 6.88 (d, J=2.0 Hz, 1H), 6.79–6.74 (m, 2H), 4.23 (t, J=6.5 Hz, 2H), 4.04 (d, J=15.5 Hz, 1H), 3.87 (s, 3H), 3.78 (d, J=15.5 Hz, 1H), 3.61 (t, J=6.5 Hz, 2H); MS (ESI) m/z 532.7 (M+H)$^+$; HPLC $t_R$ 8.38 min.

D. 4-(4-(2-Bromoethoxy)-benzyl)-3-(2,4-dichlorophenyl)-7-hydroxy-chromen-2-one

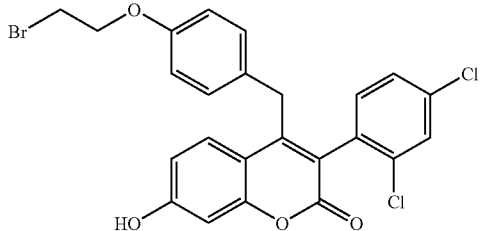

A mixture of 4-(4-(2-bromoethoxy)-benzyl)-3-(2,4-dichlorophenyl)-7-methoxy-chromen-2-one (4.0 g, 7.49 mmol), AlCl$_3$ (5.89 g, 44.2 mmol), and EtSH (2.77 mL, 37.4 mmol) in $CH_2Cl_2$ (200 mL) was stirred at room temperature for 2.5 h. The mixture was slowly poured into $CH_2Cl_2$/sat. aq NaHCO$_3$. The resultant layers were separated, and the aqueous phase was further extracted with $CH_2Cl_2$ (3×). The aqueous layer was raised to pH 10 with aqueous 2M NaOH and extracted with AcOEt (3×). Each organic layer was washed with brine and dried ($MgSO_4$), and the combined organic phases were concentrated in vacuo. The resultant residue was purified using flash chromatography (250 g silica gel, 95:5→9:1 $CH_2Cl_2$:AcOEt) to afford the title compound, which was isolated as an off-white solid (3.454 g, 89%). $^1$H NMR (300 MHz, CDCl$_3$) δ 7.50 (d, J=2.0 Hz, 1H), 7.42 (d, J=8.8 Hz, 1H), 7.25 (dd, J=2.0, 8.0 Hz, 1H), 7.12 (d, J=8.0 Hz, 1H), 6.99 (d, J=2.0 Hz, 1H), 6.94 (d, J=8.5 Hz, 2H), 6.78 (d, J=8.5 Hz, 2H), 6.73 (dd, J=2.0, 8.8 Hz, 1H), 6.61–6.49 (br signal, 1H), 4.23 (t, J=6.0 Hz, 2H), 4.04 (d, J=15.5 Hz, 1H), 3.78 (d, J=15.5 Hz, 1H), 3.61 (t, J=6.0 Hz, 2H); MS (ESI) m/z 516.9 (M–H)$^-$; HPLC $t_R$ 7.41 min.

E. 4-(4-(2-Bromoethoxy)-benzyl)-3-(2,4-dichlorophenyl)-7-hydroxy-8-iodo-chromen-2-one

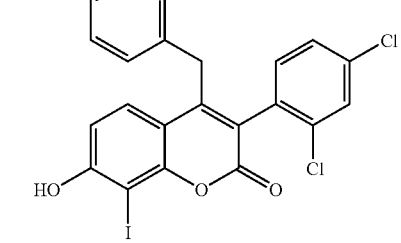

To a solution of 4-(4-(2-Bromoethoxy)-benzyl)-3-(2,4-dichlorophenyl)-7-hydroxy-chromen-2-one (2.734 g, 5.26 mmol) in NH$_4$OH (22 mL), MeOH (55 mL) and $CH_2Cl_2$ (33 mL) was added I$_2$ (1.334 g, 5.26 mmol), and the resulting mixture was stirred at r.t for 30 min. Aqueous 4 M HCl was then added to lower the pH of the aqueous layer to 5. The resultant layers were separated and the aqueous phase was extracted with AcOEt (3×). The combined organic layers were washed with brine (2×), dried (MgSO$_4$) and concentrated in vacuo. The residual beige solid (3.25 g, 96%) was used directly in the next step without further purification. $^1$H NMR (300 MHz, DMSO) δ 11.43 (s, 1H), 7.74 (d, J=2.0 Hz, 1H), 7.51–7.42 (m, 3H), 7.02 (d, J=8.5 Hz, 2H), 6.82 (d, J=8.8 Hz, 1H), 6.78 (d, J=8.5 Hz, 2H), 4.21 (t, J=5.0 Hz, 2H), 4.04 (d, J=15.5 Hz, 1H), 3.73 (t, J=5.0 Hz, 2H), 3.70 (d, J=15.5 Hz, 1H); MS (ESI) m/z 642.7 (M–H)$^-$; HPLC $t_R$ 7.27 min.

F. 3-(2,4-Dichlorophenyl)-7-hydroxy-8-iodo-4-(4-(2-pyrrolidin-1-yl-ethoxy)-benzyl)-chromen-2-one

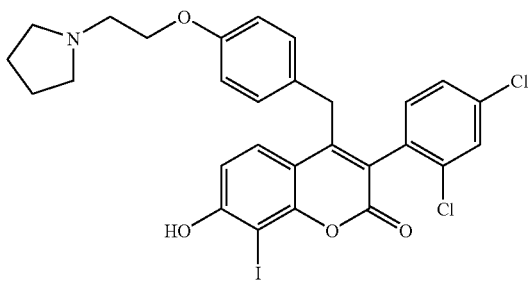

To a stirred suspension 4-(4-(2-Bromoethoxy)-benzyl)-3-(2,4-dichlorophenyl)-7-hydroxy-8-iodo-chromen-2-one (1.90 g, 2.94 mmol) in anhydrous THF (20 mL) was added pyrrolidine (1.46 mL, 17.6 mmol), and the resulting yellow solution was heated at 85° C. for 1.5 h. The resultant mixture was cooled to room temperature and the solvent was removed in vacuo. The resultant residue was dissolved in $CH_2Cl_2$, washed with H$_2$O and brine and dried (MgSO$_4$). The organic phase was concentrated in vacuo. The resultant residue was purified using flash chromatography (200 g silica gel, 12:1→9:1→85:15 $CH_2Cl_2$:MeOH) to afford the title compound as a yellow solid (1.87 g, 100%). ¹H NMR (300 MHz, CDCl₃) δ 7.50 (d, J=2.0 Hz, 1H), 7.32 (d, J=8.8 Hz, 1H), 7.26 (dd, J=2.0, 8.0 Hz, 1H), 7.12 (d, J=8.0 Hz, 1H), 6.95–6.86 (m, 3H), 6.77–6.70 (m, 2H), 4.30 (t, J=5.0 Hz, 2H), 4.00 (d, J=15.5 Hz, 1H), 3.76 (d, J=15.5 Hz, 1H), 3.25 (t, J=5.0 Hz, 2H), 3.19–3.04 (m, 4H), 2.04–1.91 (m, 4H); MS (ESI) m/z 635.6 (M)⁺; HPLC t$_R$ 5.85 min.

G. 3-(2,4-Dichlorophenyl)-7-hydroxy-8-methyl-4-(4-(2-pyrrolidin-1-yl-ethoxy)-benzyl)-chromen-2-one

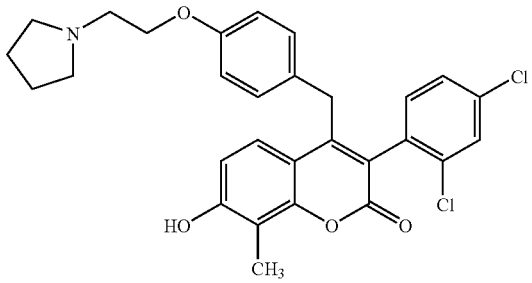

A mixture of 3-(2,4-dichlorophenyl)-7-hydroxy-8-iodo-4-(4-(2-pyrrolidin-1-yl-ethoxy)-benzyl)-chromen-2-one (1.85 g, 2.91 mmol), K₂CO₃ (1.21 g, 8.75 mmol), trimethylboroxine (427 µL, 3.05 mmol) and Pd(Ph₃P)₄ (336 mg, 0.29 mmol) in anhydrous dioxane (22 mL) was stirred at reflux temperature for 2.5 h. After cooling the resultant green suspension to room temperature, the solvent was removed in vacuo. The resultant residue was dissolved in CH₂Cl₂, and the organic layer was washed with H₂O and brine, dried (MgSO₄) concentrated in vacuo. The resultant residue was purified using flash chromatography (125 g silica gel, 8:0.5:0.5→7:0.5:0.5 CH₂Cl₂:MeOH:AcOEt→9:1 CH₂Cl₂:MeOH) to afford a yellow solid that was further purified using reverse phase HPLC (followed by an extraction with CH₂Cl₂/NaHCO₃). The title compound was isolated as a yellow solid (220.4 mg, 14%). ¹H NMR (300 MHz, CDCl₃) δ 7.48 (d, J=2.0 Hz, 1H), 7.24 (dd, J=2.0, 8.0 Hz, 1H), 7.18 (d, J=8.8 Hz, 1H), 7.12 (d, J=8.0 Hz, 1H), 6.90 (d, J=8.8 Hz, 2H), 6.84 (d, J=8.8 Hz, 1H), 6.72 (d, J=8.8 Hz, 2H), 4.23 (t, J=5.0 Hz, 2H), 4.00 (d, J=15.5 Hz, 1H), 3.74 (d, J=15.5 Hz, 1H), 3.24 (t, J=5.0 Hz, 2H), 3.15–3.04 (m, 4H), 2.20 (s, 3H), 2.05–1.93 (m, 4H); MS (ESI) m/z 523.8 (M)⁺; HPLC t$_R$ 4.74 min.

5.4 Example 4

Synthesis of 8-acetyl-3-(2,4-dichlorophenyl)-7-hydroxy-4-(4-(2-pyrrolidin-1-yl-ethoxy)-benzyl)-chromen-2-one

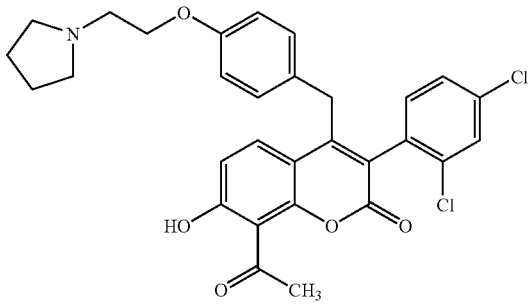

Steps A–F were carried out as described in Example 3, above, and step G was replaced with steps H and I, below.

H. A mixture of 3-(2,4-dichlorophenyl)-7-hydroxy-8-iodo-4-(4-(2-pyrrolidin-1-yl-ethoxy)-benzyl)-chromen-2-one (187 mg, 0.294 mmol), tributyl(1-ethoxyvinyl)tin (119 µL, 0.353 mmol) and Pd(Ph₃P)₄ (34 mg, 0.0294 mmol) in anhydrous dioxane (6 mL) was stirred at reflux temperature for 2 h. After cooling to room temperature, aqueous 1M HCl was added, and the resulting mixture was stirred for 20 min. CH₂Cl₂ was added and the layers were separated. The aqueous layer was further extracted with CH₂Cl₂ (2×). The combined organic layers were dried (MgSO₄) and concentrated in vacuo. The resultant residue was purified using flash chromatography (silica gel, 19:1→9:1 CH₂Cl₂:MeOH) to afford a light brown solid (48 mg, 84% pure by HPLC) that was recrystallized from AcOEt/hexane to provide the title compound as a yellow solid (22 mg, 14%).

I. The product of step H was dissolved in a mixture of 2-propanol/concentrated HCl. After stirring at room temperature for 20 min, the solvents were evaporated. The resultant solid was triturated in Et₂O and filtered to provide 12 mg of the title compound in the form of its HCl salt. ¹H NMR (300 MHz, DMSO) δ 11.57 (s, 1H), 10.05–9.91 (br signal, 1H), 7.72 (d, J=2.0 Hz, 1H), 7.56 (d, J=8.8 Hz, 1H), 7.48 (dd, J=2.0, 8.0 Hz, 1H), 7.44 (d, J=8.0 Hz, 1H), 7.04 (d, J=8.5 Hz, 2H), 6.86–6.78 (m, 3H), 4.20 (t, J=4.5 Hz, 2H), 4.02 (d, J=15.5 Hz, 1H), 3.73 (d, J=15.5 Hz, 1H), 3.60–3.45 (m, 4H), 3.25–2.97 (m, 2H), 2.58 (s, 3H), 2.05–1.75 (m, 4H); MS (ESI) m/z 552.0 (M+H)⁺; HPLC t$_R$ 5.33 min 5.5 Example 5

Synthesis of 3-(4-chlorophenyl)-7-hydroxy-8-iodo-4-{(4-(2-piperidylethoxy)phenyl)methyl}2H-chromen-2-one

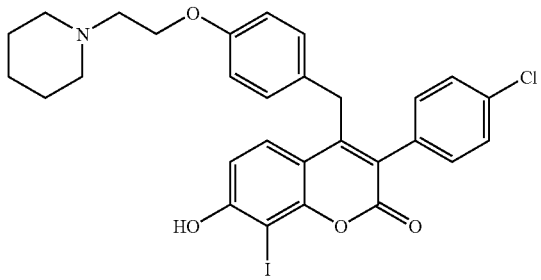

To a solution containing 3-(4-chlorophenyl)-7-hydroxy-4-{(4-(2-piperidylethoxy)phenyl)methyl}-2H-chromen-2-one (0.500 g.) in methanol (10 mL) was added ammonium hydroxide (3 mL) and elemental iodine (0.259 g.). The reaction mixture was allowed to stir at room temperature for 10 minutes. The solvent was removed under reduced pressure. The resulting solid was extracted with methylene chloride (3×) and water. The organic layers were combined and dried over magnesium sulfate. The magnesium sulfate was filtered, and the solvent was removed under reduced pressure to afford a yellow solid. The solid was purified via preparative HPLC (20–50% acetonitrile/water, 20 mL/min.) to afford the title compound (0.290 g., 46% yield). ¹H-NMR (CDCl₃) δ 7.34 (dd, 3H), 7.20 (d, 2H), 6.92 (d, 2H), 6.84 (d, 1H), 6.75 (d, 2H), 4.13 (t, 2H), 3.97 (s, 2H), 2.84 (t, 2H), 2.61 (bs, 3H), 1.643 (m, 4H), 1.46 (m, 2H), 1.24 (m, 1H). MS (m/z) 616 (M+1)⁺.

5.6 Example 6

Synthesis of 3-(4-chlorophenyl)-7-hydroxy-2-oxo-4-{(4-(2-piperidylethoxy)phenyl}-2H-chromen-8-carbonitrtile-2-one

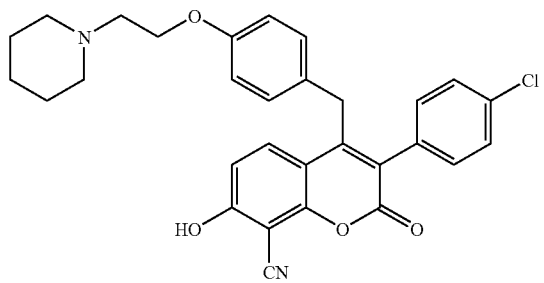

To a solution of 3-(4-chlorophenyl)-7-hydroxy-8-iodo-4-{(4-(2-piperidylethoxy)phenyl)methyl}-2H-chromen-2-one (prepared as described above in Example 5) (1.50 g) in dimethyl formamide (30 mL) was added copper cyanide (1.05 g.). The solution was heated in a screw-capped flask at 120° C. for 18 hours. After cooling to room temperature, the solvent was removed under reduced pressure. The resultant oil was extracted with methylene chloride and water. The organic layers were combined and dried over magnesium sulfate. The magnesium sulfate was filtered, and the solvent was removed under reduced pressure. The crude solid was purified via preparative HPLC (30–65% acetonitrile/water, 20 mL/min., 30 min.) to afford the title compound (0.125 g, 10% yield). MS (m/z) 515 (M+1)$^+$.

5.7 Example 7

Synthesis of 7-hydroxy-8-prop-2-enyl-4-{(4-(2-pyrrolidinylethoxy)phenyl)methyl}-3-(4-(trifluoromethyl)phenyl)-2H-chromen-2-one

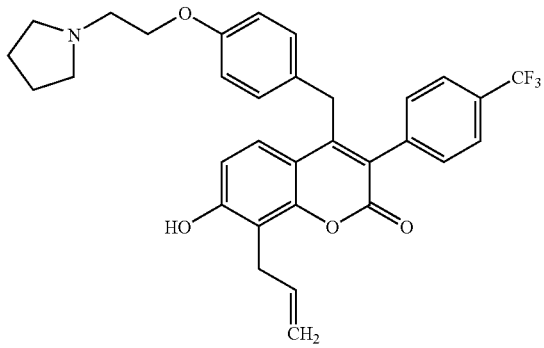

A. 7-Prop-2-enyloxy-4-{(4-(2-pyrrolidinylethoxy)phenyl)methyl}-3-(4-(trifluoromethyl)Phenyl)-2H-chromen-2-one To a solution containing 7-hydroxy-4-{(4-(2-pyrrolidinylethoxy)phenyl)methyl}-3-(4-(trifluoromethyl)phenyl)-2H-chromen-2-one (0.550 g.) in tetrahydrofuran (6 mL) and methylene chloride (6 mL) was added allyl alcohol (0.226 mL) and triphenylphosphine (0.641 g.). Diisopropylazodicarboxylate (0.437 mL) was then added dropwise to the solution. The resultant mixture was allowed to stir for about one hour (or until the starting material was consumed). The solution was concentrated under reduced pressure and extracted with methylene chloride (3×) and water. The organic layers were dried over magnesium sulfate, the magnesium sulfate was filtered and the solvent was concentrated under reduced pressure to provide an orange oil. The oil was purified via silica gel chromatography (6–10% methanol/methylene chloride) to afford 7-prop-2-enyloxy-4-{(4-(2-pyrrolidinylethoxy)phenyl)methyl}-3-(4-(trifluoromethyl) Phenyl)-2H-chromen-2-one (0.245 g., 40% yield). MS (m/z) 550 (M+1)$^+$.

B. 7-Hydroxy-8-prop-2-enyl-4-{(4-(2-pyrrolidinylethoxy)phenyl)methyl}-3-(4-(trifluoromethyl)phenyl-2H-chromen-2-one 7-Prop-2-enyloxy-4-{(4-(2-pyrrolidinylethoxy)phenyl)methyl}-3-(4-(trifluoromethyl) Phenyl)-2H-chromen-2-one (0.150 g.) was dissolved in diethylaniline (4 mL) and allowed to stir at 190° C. for two hours. The resultant solution was extracted with methylene chloride (3×) and 1M hydrochloric acid. The organic layers were dried over sodium sulfate and filtered, and the solvent was removed under reduced pressure to afford a crude brown solid. The solid was purified via preparative-HPLC (40–100% acetonitrile/water, 20 mL/min.) to afford the title compound (0.027 g, 18% yield). $^1$H-NMR (CDCl$_3$) δ 7.63 (d, 2H), 7.38 (d, 2H), 7.25 (d, 1H), 6.92 (d, 2H), 6.75 (d, 2H), 6.70 (d, 1H), 6.0 (m, 1H), 5.13 (dd, 2H), 4.12 (t, 2H), 3.94 (s, 2H), 3.66 (d, 2H), 3.05 (bs, 2H), 2.8 (bs, 4H), 1.25 (s, 2H). MS (m/z) 550 (M+1)$^+$.

5.8 Example 8

Synthesis of 8-((dimethylamino)methyl)-3-(4-chlorophenyl)7-hydroxy-4-{(-(2-piperidylethoxy)phenyl)methyl}-2H-chromen-2-one

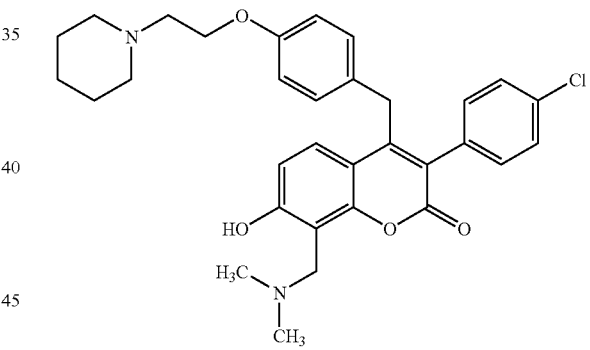

To a solution containing 37% formaldehyde in water (0.414 mL) was added 2.0M dimethylaniline (2.5 mL). The solution was allowed to stir at room temperature for fifteen minutes and it was added to 7-hydroxy-4-{(4-(2-pyrrolidinylethoxy)phenyl)methyl}-3-(4-(trifluoromethyl)phenyl)-2H-chromen-2-one (0.250 g) dissolved in methanol (5 mL) and methylene chloride (2 mL). The resultant mixture was heated to 70° C. for about three hours (or until no visible starting material was detected via thin layer chromatography). The solvent was removed under reduced pressure, and the resultant oil was extracted with methylene chloride (3×) and sodium bicarbonate solution. The organic layers were combined and dried over magnesium sulfate, the magnesium sulfate was filtered and the solvent was removed under reduced pressure. The resultant oil was purified via preparative-HPLC (20–50% acetonitrile/water, 20 mL/min., 30 min.) to afford the title compound 0.130 g., 46% yield). $^1$H-NMR (CDCl$_3$) δ 7.33 (dd, 3H), 7.18 (d, 2H), 6.93 (d, 2H), 6.78 (d, 2H), 6.75 (d, 1H), 4.05 (t, 3H), 3.94 (s, 2H), 2.74 (t, 2H), 2.48 (bs, 3H), 2.42 (s, 6H), 1.59 (m, 4H), 1.44 (m, 2H), 1.25 (m, 1H). MS (m/z) 547 (M+1)$^+$.

5.9 Example 9

6-bromo-7-hydroxy-4-(4-(2-pyrrolidin-1-yl-ethoxy)-benzyl)-3-(4-trifluoromethyl-phenyl)-chromen-2-one

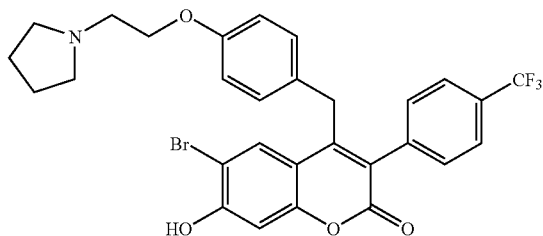

A. 1-(5-Bromo-2-hydroxy-4-methoxy-phenyl)-2-(4-hydroxy-phenyl)-ethanone

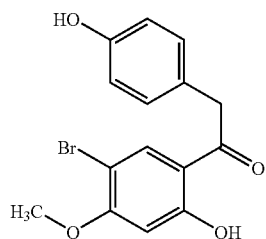

A solution of bromine (3.6 mL, 75.6 mmol) in acetic acid (50 mL) was added dropwise to a stirring solution of 1-(2-hydroxy-4-methoxy-phenyl)-2-(4-hydroxy-phenyl)-ethanone (20 g, 77.4 mmol) in acetic acid (500 mL), and the reaction mixture was allowed to stir for 8 h. The acetic acid was then removed under reduced pressure, and the resulting solid was recrystallized from methanol/water to provide 8.9 g of crude product. Further purification using reverse-phase preparatory HPLC (30–100% acetonitrile+0.1% TFA in $H_2O$+0.1% TFA, over 18 min, then at 100% acetonitrile for 15 min) provided fractions that were subsequently neutralized with sodium bicarbonate and extracted using ethyl acetate. The organic fractions were combined, dried over magnesium sulfate and filtered, and the solvent was removed under reduced pressure to afford the title compound (4.8 g, 18%). MS (ESI) m/z 337.3 (M+1)$^+$, 339.3 (M+1+2)$^+$.

B. 6-Bromo-4-(4-hydroxy-benzyl)-7-methoxy-3-(4-trifluoromethyl-phenyl)-chromen-2-one

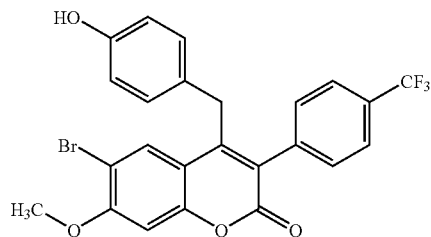

A mixture of 1-(5-bromo-2-hydroxy-4-methoxy-phenyl)-2-(4-hydroxy-phenyl)-ethanone (0.64 g, 1.9 mmol), 4-trifluoromethylphenylacetic acid (0.78 g, 3.8 mmol), carbonyl diimidazole (0.62 g, 3.8 mmol), N,N-dimethylaminopyridine (0.12 g, 1.0 mmol), and potassium carbonate (0.52 g, 3.8 mmol) in DMF (15 mL) was heated within an 80° C. oil bath overnight. The cooled reaction mixture was poured into water and extracted with EtOAc. Organic extracts were combined and washed with water and saturated sodium chloride in succession, dried over magnesium sulfate, filtered and concentrated under reduced pressure. The resulting material purified using silica gel flash column chromatography (1:2 EtOAc:hexanes) to provide the title compound (0.82 g, 85%). MS (ESI) m/z 505.0 (M+1)$^+$, 507.0 (M+1+2)$^+$.

C. 6-Bromo-7-methoxy-4-(4-(2-pyrrolidin-1-yl-ethoxy)-benzyl)-3-(4-trifluoromethyl-phenyl)-chromen-2-one

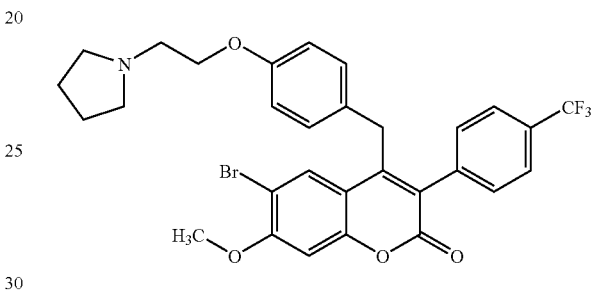

To a solution of 6-bromo-4-(4-hydroxy-benzyl)-7-methoxy-3-(4-trifluoromethyl-phenyl)-chromen-2-one (0.70 g, 1.4 mmol) and triphenylphosphine (0.73 g, 2.8 mmol) in THF (40 mL) were sequentially added 1-(2-hydroxyethyl)pyrrolidine (0.65 mL, 5.6 mmol) and diisoproyl azodicar-oxylate (0.55 mL, 2.8 mmol). The reaction mixture was allowed to stir at room temperature overnight. The reaction mixture was poured into water and extracted with EtOAc. Organic extracts were combined and washed with water and saturated sodium chloride in succession, dried over magnesium sulfate, filtered and concentrated under reduced pressure. Purification using silica gel flash column chromatography (10% methanol in $CH_2Cl_2$) provided the title compound as a solid (0.44 g, 53%). MS (ESI) m/z 602.3 (M+1)$^+$, 604.3 (M+1+2)$^+$.

D. 6-Bromo-7-hydroxy-4-(4-(2-pyrrolidin-1-yl-ethoxy)-benzyl)-3-(4-trifluoromethyl-phenyl)-chromen-2-one

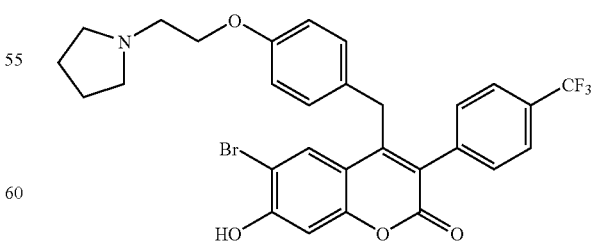

A solution of 6-bromo-7-methoxy-4-(4-(2-pyrrolidin-1-yl-ethoxy)-benzyl)-3-(4-trifluoromethyl-phenyl)-chromen-2-one (0.20 g, 0.3 mmol) and hydrogen bromide in acetic acid (10 mL) was heated to reflux overnight. After cooling, excess acetic acid was removed under reduced pressure. The resulting residue was dissolved in ethyl acetate and washed with saturated sodium bicarbonate, water, and saturated sodium chloride in succession; dried over magnesium sulfate; filtered; and concnetrated under reduced pressure to afford crude product. Purification using reverse-phase preparatory HPLC (20–80% acetonitrile+0.1% TFA in $H_2O$+ 0.1% TFA, over 30 min) provided fractions that were subsequently neutralized with sodium bicarbonate and extracted using ethyl acetate. The organic fractions were combined, dried over magnesium sulfate, filtered, and concentrated under reduced pressure to afford the title compound (>98% pure, 45.0 mg, 23%). $^1$H NMR (300 MHz, $d_6$-DMSO) δ 7.78 (m, 2H), 7.69 (s, 1H), 7.55 (m, 2H), 7.08 (m, 2H), 6.88 (s, 1H), 6.83 (m, 2H), 4.04 (t, 2H), 3.94 (s, 2H), 2.92 (t, 2H), 2.67 (bm, 4H), 1.72 (bm, 4H). MS (ESI) m/z 588.3 (M+1)$^+$, 590.3 (M+1+2)$^+$.

Example 10

Additional Representative Benzopyranone Compounds

Table 1, below, discloses representative Benzopyranone Compounds. These Benzopyranone Compounds can be obtained using the methods disclosed herein.

TABLE 1

Representative Benzopyranone Compounds

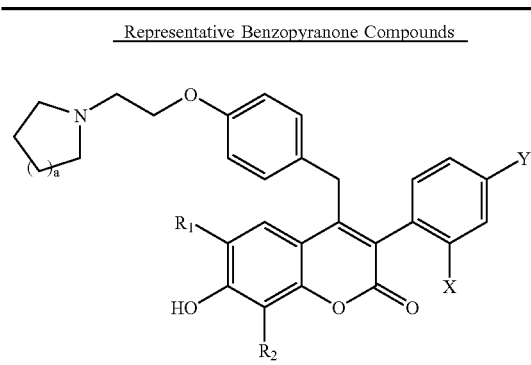

(I)

and pharmaceutically acceptable salts thereof, wherein:

| No. | $R_1$ | $R_2$ | X | Y | n |
|---|---|---|---|---|---|
| 1 | H | C(=O)CH$_3$ | Cl | Cl | 1 |
| 2 | CH$_3$ | H | Cl | Cl | 1 |
| 3 | H | CH$_3$ | Cl | Cl | 1 |
| 4 | H | CH$_3$ | H | CF$_3$ | 1 |
| 5 | CH$_3$ | H | H | CF$_3$ | 1 |
| 6 | C(=O)CH$_3$ | H | H | CF$_3$ | 1 |
| 7 | H | C(=O)CH$_3$ | H | CF$_3$ | 1 |
| 8 | H | CN | H | CF$_3$ | 1 |
| 9 | Br | H | H | CF$_3$ | 1 |
| 10 | H | I | H | Cl | 2 |
| 11 | —CH(OH)CH$_3$ | H | CF$_3$ | H | 1 |

Example 11

Inhibition of IL-6 Release

Illustrative Benzopyranone Compounds were tested for their ability to inhibit IL-6 release from human U-2 OS osteosarcoma cells stably transfected with human ER-α or ER-β. (Stein, B.; Yang, M. X. *Mol. Cell. Biol* 15: 4971–4979, 1995; Poli, V. et. al., *EMBO J*. 13:1189–1196, 1994). As a control, IL-6 release was determined from the parental non-transfected U-2 OS cell line, which does not express detectable levels of ER-α or ER-β. Benzopyranone Compounds having an IC$_{50}$<100 nM are particularly useful as bone resorption inhibitors in vivo. Accordingly, the Benzopyranone Compounds, are particularly useful for the treatment of osteoporosis, Paget's disease and metastatic bone cancer. These Benzopyranone Compounds are also useful as anti-cancer agents, since elevated IL-6 levels are responsible for certain cancers such as multiple myeloma, prostate cancer, ovarian cancer, renal carcinoma and cervical carcinoma.

Human U-2 OS osteosarcoma cells (ATCC) were stably transfected with expression vectors for human full-length ER-α or ER-β using standard molecular biology techniques. Stable subclones were generated that expressed high levels of ER-α or ER-β mRNA. The expression of ER-α or ER-β was confirmed using RNase protection analysis. The parental U-2 OS cells did not express any measurable amounts of ER-α or ER-β.

Cells were plated into 96-well plates at a density of 80,000 cells per well in phenol red-free media with charcoal-stripped fetal calf serum. Twenty four hours later, cells were either treated with vehicle (0.2% DMSO) or a Benzopyranone Compound (0.01–1000 nm in 0.2% DMSO). Thirty minutes later cells were stimulated with 2.5 ng/ml TNFα and 1 ng/ml IL-1β. Twenty-four hours later the media supernatant was analyzed for cytokine production (IL-6) using commercially available ELISA kits following the manufacturer's instructions. Cytokine production in the presence of vehicle (0.2% DMSO) was set to 100%.

The results (Table 2) are expressed as an IC$_{50}$ (nM) value which is the concentration of the Benzopyranone Compound sufficient to inhibit the production of IL-6 50% relative to the amount of IL-6 produced in the presence of vehicle. The results show that illustrative Benzopyranone Compounds inhibit the release of IL-6 and, accordingly, are useful for treating or preventing a bone-resorbing disease.

Example 12

Inhibition of MCF-7 Breast Cancer Cell Proliferation

This example shows the ability of illustrative Benzopyranone Compounds to inhibit 17β-estradiol-dependent growth of MCF-7 breast cancer cells in vitro and compares their activity to that of reference SERMs. MCF-7 cells represent an excellent in vitro system to study the effects of compounds on estrogen-dependent breast cancer growth. (May, F. E. B.; Westley, B. R. *J. Biol. Chem.* 262:15894–15899, 1987). Benzopyranone Compounds having an IC$_{50}$<100 nM are particularly useful as anti-breast cancer agents in vivo.

MCF-7 breast carcinoma cells were plated in 24-well dishes at a density of 5×10$^3$ cells/well in phenol-red free DMEM:F-12 (1:1) medium containing 1% antibiotics, 0.05% mercaptoethanol, 0.01% ethanolamine, 0.42 ng/mL sodium selenite and 5% charcoal-stripped FCS.

Illustrative Benzopyranone Compounds (0.1–1000 nM in 0.2% DMSO) and 0.1 nM 17β-estradiol were added to the cultured MCF-7 breast cancer cells for 72 h. Subsequently, $^3$H-labeled thymidine was added and its incorporation into cells was measured following 4 h incubation. The results (Table 2) are expressed as an IC$_{50}$ (nM) value which is the concentration of the Benzopyranone Compound sufficient to inhibit the growth of MCF-7 breast cancer cells by 50% relative to controls. The results show that the illustrative Benzopyranone Compounds inhibit MCF-7 breast cancer cell proliferation and, accordingly, are useful for treating or preventing breast cancer in a patient.

TABLE 2

In vitro data

| Structure | U2 OS (ER-α) | IC$_{50}$ (nM) U2 OS (ER-β) | MCF-7 |
|---|---|---|---|
| (pyrrolidine-ethoxy-benzyl / 6-methyl-7-hydroxy-3-(4-CF₃-phenyl)-coumarin) | 13.3 | >1000 | 59.5 |
| (pyrrolidine-ethoxy-benzyl / 6-acetyl-7-hydroxy-3-(4-CF₃-phenyl)-coumarin) | 850/>1000 | >1000 | >1000 |
| (pyrrolidine-ethoxy-benzyl / 6-(1-hydroxyethyl)-7-hydroxy-3-(4-CF₃-phenyl)-coumarin) | 850/>1000 | >1000 | — |
| (pyrrolidine-ethoxy-benzyl / 6-bromo-7-hydroxy-3-(4-CF₃-phenyl)-coumarin) | 310/>1000 | >1000 | >1000 |
| (pyrrolidine-ethoxy-benzyl / 6-methyl-7-hydroxy-3-(2,4-dichlorophenyl)-coumarin) | 1.7 | >1000 | 10 |
| (pyrrolidine-ethoxy-benzyl / 7-hydroxy-8-methyl-3-(4-CF₃-phenyl)-coumarin) | 55.5 | <1000 | 235 |

TABLE 2-continued

In vitro data

| Structure | U2 OS (ER-α) | IC$_{50}$ (nM) U2 OS (ER-β) | MCF-7 |
|---|---|---|---|
| (pyrrolidine-ethoxy-phenyl-CH2 / 3-(2,4-dichlorophenyl)-7-hydroxy-8-methyl-coumarin) | 6.9 | <1000 | 35 |
| (pyrrolidine-ethoxy-phenyl-CH2 / 3-(4-CF3-phenyl)-7-hydroxy-8-acetyl-coumarin) | 39 | <1000 | 185 |
| (pyrrolidine-ethoxy-phenyl-CH2 / 3-(2,4-dichlorophenyl)-7-hydroxy-8-acetyl-coumarin) | 5.0 | <1000 | 112.5 |
| (pyrrolidine-ethoxy-phenyl-CH2 / 3-(4-chlorophenyl)-7-hydroxy-8-methyl-coumarin) | 285 | <1000 | <1000 |
| (pyrrolidine-ethoxy-phenyl-CH2 / 3-(4-CF3-phenyl)-7-hydroxy-8-cyano-coumarin) | 390 | >1000 | — |

Accordingly, the in vitro results of Examples 11 and 12 as illustrated in Table 2, above, show that the Benzopyranone Compounds are useful for the treatment or prevention of a bone-resorbing disease and cancer.

Example 13

Inhibition of BG-1 Ovarian Carcinoma Cell Proliferation

This assay is useful to demonstrate the ability of illustrative Benzopyranone Compounds to inhibit 17β-estradiol-dependent growth of BG-1 ovarian carcinoma cells in vitro and compares their ability to that of reference SERMs. BG-1 cells serve as a useful in vitro model for the evaluation of the effects of antiestrogenic compounds on ovarian tumor growth (Greenberger, L. M. et. al., *Clin. Cancer Res.* 7:3166–3177, 2001).

BG-1 ovarian carcinoma cells are plated in 24-well dishes at a density of $5 \times 10^3$ cells/well in phenol-red free DMEM: F-12 (1:1) medium containing 1% antibiotics, 0.05% mercaptoethanol, 0.01% ethanolamine, 0.42 ng/mL sodium selenite and 5% charcoal-stripped FCS. Illustrative Benzopyranone Compounds (0.1–1000 nM in 0.2% DMSO) and 0.1 nM 17β-estradiol are added to the cultured BG-1 ovarian carcinoma cells and incubated for 72 h. Subsequently, $^3$H-labeled thymidine is added and its incorporation into cells is measured following 4 h incubation. The results are expressed as an $IC_{50}$ (nM) value, which is the concentration of the Benzopyranone Compound necessary to inhibit the growth of BG-1 ovarian carcinoma cells by 50% relative to controls. The ability of illustrative Benzopyranone Compounds to inhibit the growth of BG-1 ovarian cancer cells will indicate that they are useful for treating or preventing ovarian cancer in a patient.

Example 14

Rat Pharmacokinetic (PK) Analysis

Rat PK Cassette Standard Assay

An illustrative Benzopyranone Compound and an internal standard raloxifene are administered to a rat via oral gavage at a dose level of 5 mg/kg body weight. Blood is sampled over the time period from 15 min to 24 h postdose. Blood samples are prepared by acetonitrile precipitation, centrifuged, and supernatants are evaporated in a vacuum centrifuge. Dried residuals are dissolved in methanol/water (60:40 v/v) containing 1% formic acid and analyzed by HPLC on an UPTISPHERETM C18 reversed-phase HPLC column (particle size: 3 μm; column dimensions: 2×50 mm). Eluent A is 10% acetonitrile in water with 0.1% formic acid (pH 2.1), eluent B is 90% acetonitrile with 10% water and 0.1% formic acid (pH 2.1). A linear gradient is run from 5 to 100% B over 7 min followed by a 3 min hold at 100% B at a constant temperature of 50° C. in the column compartment. The flow rate is held constant at 0.4 mL/min. Sample injection volume is 10 μL. The flow from the HPLC system is directly introduced into the ion source of an Agilent 1100 series MS-detector (single quadrupole mass analyzer) and subjected to atmospheric pressure electrospray ionization (positive mode). All compounds are detected as protonated quasi-molecular ions $(M+H)^+$. Raloxifene is used as an analytical internal standard. Quantification of blood levels of the compounds is based on a 7-level calibration curve (in triplicate) using blank rat blood samples to which have been added stock solutions of external and internal standards.

Rat PK Cassette Validation

Raloxifene alone is administered p.o. (3 mg/kg) to four female rats each. Blood samples are collected and analyzed as described above. The pharmacokinetic data generated from this validation study are compared with the data for raloxifene obtained in cassette dosing experiments to check for potential pharmacokinetic interactions. Deviations exceeding the typical range of biological variability (approx. ±50% max. for individual parameters) are considered strongly indicative for pharmacokinetic interactions between compounds in the cassette, and the respective data are discarded.

Example 15

Pharmacokinetic Profile of an Illustrative Benzopyranone Compound in Cynomolgus Monkeys After Intravenous and Oral Administration A Benzopyranone Compound is administered at 0.5 mg·kg$^{-1}$ i.v. and 1.0 mg·kg$^{-1}$ p.o. For i.v. administration, 10 mg of the compound is dissolved in 0.4 mL 1-methyl-2-pyrrolidone and adjusted to 2 mL with PEG 200, resulting in a concentration of 5 mg·mL$^{-1}$.

The Benzopyranone Compound is administered orally as a suspension. The suspension is prepared by dissolving 20 mg of the compound in approx. 18 mL of a solution of 2.5% (w/v) malic acid in 1.0% hydroxypropyl cellulose (HPC, w/v). Thereafter, the pH is adjusted with 1 N NaOH to pH 4.5 and the volume is adjusted to 20 mL. This results in a final concentration of the test compound of 1.0 mg·mL$^{-1}$.

The Benzopyranone Compound is injected intravenously into a saphenous vein (injection volume 0.1 mL·kg$^{-1}$, injection time approx. 30 sec). Oral administration is performed with a feeding tube (application volume 1 mL·kg$^{-1}$, flushed with 10 ml water). The Benzopyranone Compound is given to 2 animals each for each mode of administration (n=2, for i.v. and p.o.).

Blood samples (approx. 0.5 ml per time-point) will be collected from a cephalic or saphenous vein by vein puncture into EDTA-coated tubes, placed on ice immediately and stored frozen at −20° C.

Experiments are performed according to the following time schedule:
(a) blood sampling in the untreated animal (time 0, baseline);
(b) administration of test compound; and
(c) blood sampling (i.v. and p.o. administration) at 5, 15, 30, 60, 120, 180, 240, 420 minutes, 24 and 48 hours after administration.

TABLE 3

Study animals and drug treatments

| Animal | Treatment | Dose | Route |
|---|---|---|---|
| 1 | Benzopyranone Compound | 0.5 mg · kg$^{-1}$ | i.v. |
| 2 | Benzopyranone Compound | 0.5 mg · kg$^{-1}$ | i.v. |
| 3 | Benzopyranone Compound | 1.0 mg · kg$^{-1}$ | p.o. |
| 4 | Benzopyranone Compound | 1.0 mg · kg$^{-1}$ | p.o. |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference in their entirety.

What is claimed is:

1. A compound having the structure:

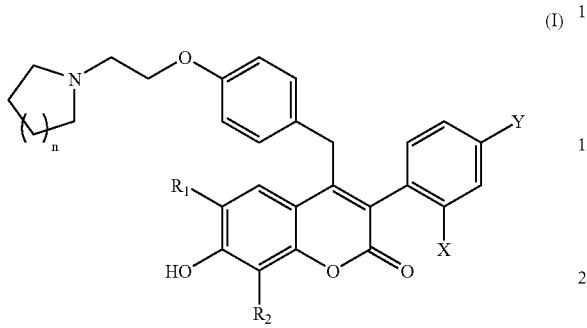

(I)

or a pharmaceutically acceptable salt thereof,
wherein:
X and Y are independently hydrogen, halogen or (halo)($C_{1-6}$alkyl);
n is 1, 2 or 3; and
either:
(a) $R_1$ is hydrogen and $R_2$ is halogen, hydroxy, —($C_{1-6}$alkyl), vinyl, —($C_{2-6}$alkynyl), —C(O)O($C_{1-6}$alkyl), -(hydroxy)($C_{1-6}$alkyl), -(amino)($C_{1-6}$alkyl), —(CH$_2$)$_m$—O—($C_{1-6}$alkyl), —C(O)($C_{1-6}$alkyl), —(CH$_2$)$_m$-phenyl, -(3- to 7-membered monocyclic heterocycle), —COOH, —C(O)H or —CN;
(b) $R_2$ is hydrogen and $R_1$ is halogen, hydroxy, —($C_{1-6}$alkyl), —($C_{2-6}$alkenyl)-($C_{2-6}$alkynyl), —C(O)O($C_{1-6}$alkyl), -(hydroxy)($C_{1-6}$alkyl), -(amino)($C_{1-6}$alkyl), —(CH$_2$)$_m$—O—($C_{1-6}$alkyl), —C(O)($C_{1-6}$alkyl), —(CH$_2$)$_m$-phenyl, -(3- to 7-membered monocyclic heterocycle), —COOH, —C(O)H or —CN; or
(c) $R_1$ and $R_2$ are —CH$_3$.

2. A compound of claim 1 wherein the compound has the structure:

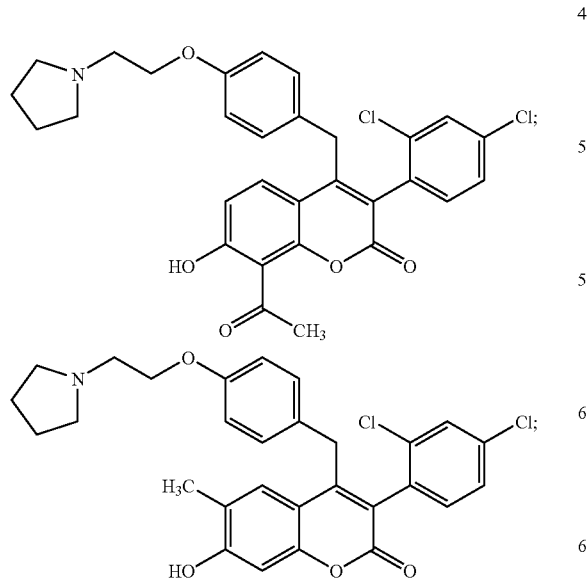

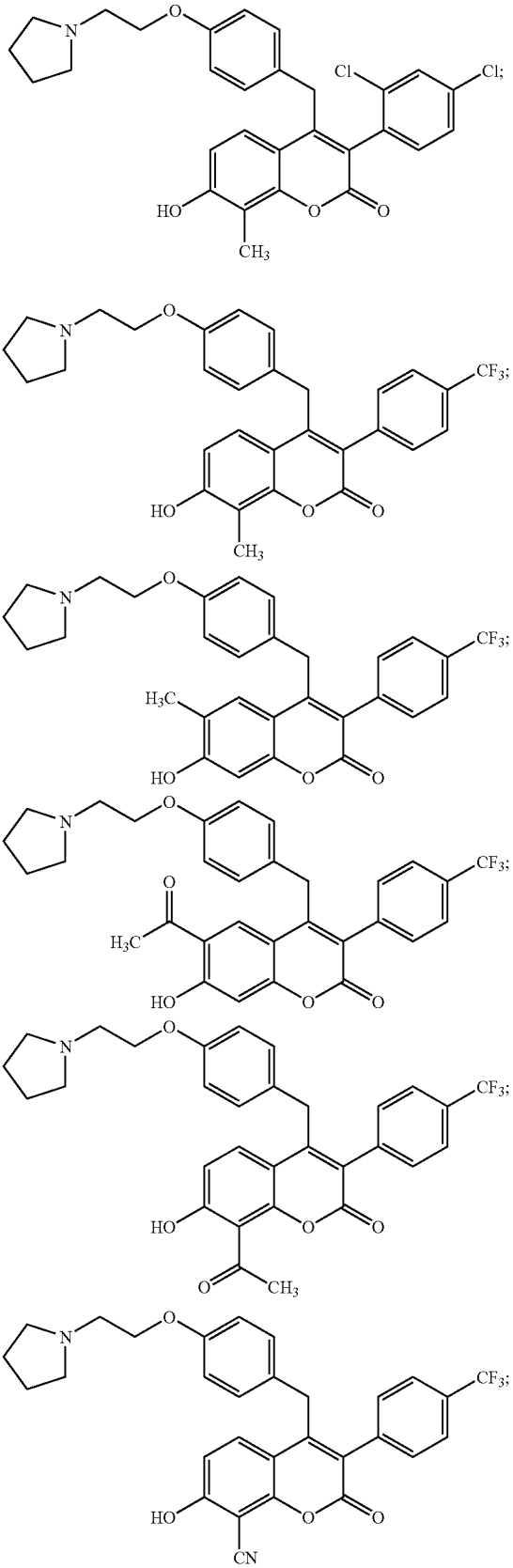

-continued

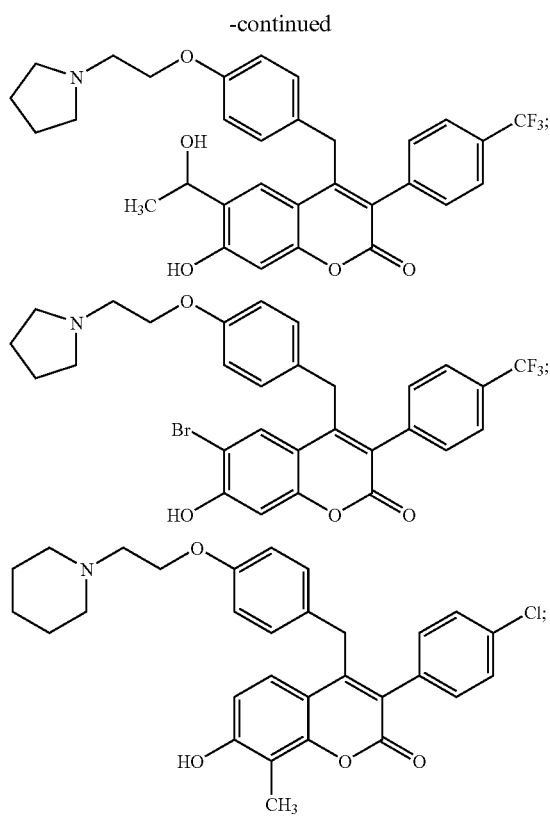

or a pharmaceutically acceptable salt thereof.

3. A method for making a compound having the structure:

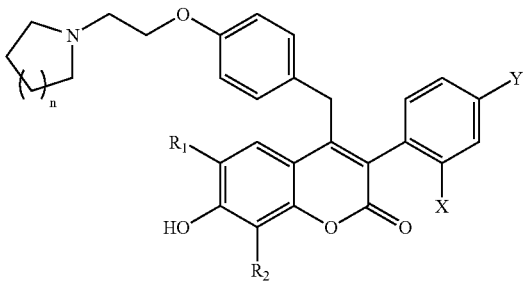
(I)

or a pharmaceutically acceptable salt thereof, comprising the step of demethylating a compound having the structure:

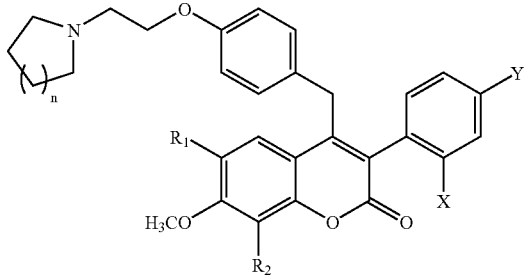
(II)

or a pharmaceutically acceptable salt thereof, wherein:

X and Y are independently hydrogen, halogen or (halo)($C_{1-6}$alkyl);

n is 1, 2 or 3; and either:

(a) $R_1$ is hydrogen and $R_2$ is halogen, hydroxy, —($C_{1-6}$ alkyl), vinyl, —($C_{2-6}$alkynyl), —C(O)O($C_{1-6}$alkyl), -(hydroxy)($C_{1-6}$alkyl), -(amino)($C_{1-6}$alkyl), —($CH_2)_m$—O—($C_{1-6}$alkyl), —C(O)($C_{1-6}$alkyl), —($CH_2)_m$-phenyl, -(3- to 7-membered monocyclic heterocycle), —COOH, —C(O)H or —CN;

(b) $R_2$ is hydrogen and $R_1$ is halogen, hydroxy, —($C_{1-6}$ alkyl), —($C_{2-6}$alkenyl)-($C_{2-6}$alkynyl), —C(O)O ($C_{1-6}$alkyl), -(hydroxy)($C_{1-6}$alkyl), -(amino)($C_{1-6}$ alkyl), —($CH_2)_m$—O—($C_{1-6}$alkyl), —C(O)($C_{1-6}$ alkyl), —($CH_2)_m$-phenyl, -(3- to 7-membered monocyclic heterocycle), —COOH, —C(O)H or —CN; or (c) $R_1$ and $R_2$ are —$CH_3$.

4. A composition comprising an effective amount of a compound or a pharmaceutically acceptable salt of the compound of claim 1 and a pharmaceutically acceptable carrier or vehicle.

* * * * *